United States Patent [19]

Suzuki et al.

[11] Patent Number: 5,136,090

[45] Date of Patent: Aug. 4, 1992

[54] BIPHENYL-5,5'-BIS-ALKANOIC ACID DERIVATIVES, THEIR PRODUCTION AND ALDOSE REDUCTASE INHIBITORS CONTAINING THE SAME

[75] Inventors: Yukio Suzuki; Kouichi Kuno; Motoshi Shoda; Masao Yaso; Satoshi Yaginuma; Akira Asahi, all of Shizuoka, Japan

[73] Assignee: Toyo Jozo Kabushiki Kaisha, Shizuoka, Japan

[21] Appl. No.: 742,354

[22] Filed: Aug. 8, 1991

[30] Foreign Application Priority Data

Aug. 8, 1990 [JP] Japan .................. 2-208127

[51] Int. Cl.$^5$ .................. C07C 59/40; A01N 37/10
[52] U.S. Cl. .................. 562/469; 549/427; 560/59
[58] Field of Search .......... 562/469; 514/570

[56] References Cited

U.S. PATENT DOCUMENTS 4,749,571  6/1988  Yaginuma et al. .......... 424/119

FOREIGN PATENT DOCUMENTS 2-72144  3/1990  Japan .

OTHER PUBLICATIONS

"Dealkylation of Esters and Cleavage of Alcoholic Carbon–oxygen Bond of Lactones with Aluminium Halide–thiol System", *Tetrahedron Letters No. 52*, by M. Node et al., pp. 5211–5214.

"Synthesis of Bitetralonyl and Bianthronyl Derivatives from Biphenyl Derivatives", *Journal of Indian Chemical Society*, vol. 42, No. 2, 1965, by K. P. Mathai et al., pp. 86–91.

*Primary Examiner*—Paul J. Killos
*Attorney, Agent, or Firm*—Young & Thompson

[57] ABSTRACT

An aldose reductase inhibitor, comprising a compound of the formula

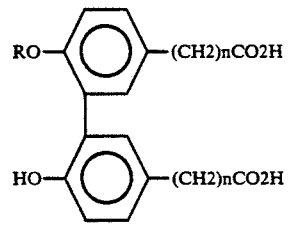

or a pharmaceutically acceptable salt thereof as the effective component, in which R denotes an alkyl of $C_{1-12}$,

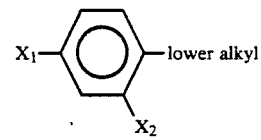

wherein $X_1$ and $X_2$ are same or different and are hydrogen or halogen, cyclohexylmethyl, cyclohexyl, tetrahydro-2H-pyran-1-yl-methyl, carboxy-lower alkyl or cyclo-lower alkyl and n is 2 or 3. These compounds exhibit a superior aldose reductase inhibiting activity with simultaneous high stability, and are for use in the prevention and therapy of diabetic complications.

2 Claims, No Drawings

BIPHENYL-5,5'-BIS-ALKANOIC ACID DERIVATIVES, THEIR PRODUCTION AND ALDOSE REDUCTASE INHIBITORS CONTAINING THE SAME

FIELD OF THE INVENTION

This invention relates to biphenyl derivatives, their production and aldose reductase inhibitors containing the same.

BACKGROUND OF THE INVENTION

Among biphenyl derivatives having an inhibiting activity for aldose reductase, there have been known aldostatin (as disclosed in Japanese Patent Appln. Kokai No. 205095/1987) and FR 900280 (as disclosed in Japanese Patent Appln. Kokai No. 72144/1990), which are now under examination for their application to the prevention or therapy of diabetic complications, such as cataracts, retinal disease, neuropathy, nephropathy and so on.

Nevertheless, there is still a need to develop substances having a higher aldose reductase inhibiting activity than those of the prior art.

The inventors have studied the pharmacodynamics of various compounds to find new aldose reductase inhibitors exhibiting superior inhibiting activity and have discovered that a series of new biphenyl derivatives represented by the following formula (I) have greater activity for inhibiting aldose reductase than aldostatin (disclosed in Kokai No. 62-205095).

SUMMARY OF THE INVENTION

Thus, the present invention provides novel biphenyl-5,5'-bis-alkanoic acid derivatives or pharmaceutically acceptable salts thereof represented by the following formula (I):

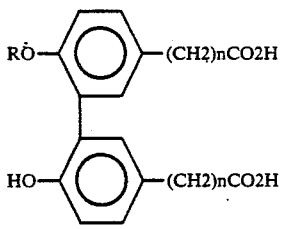
(I)

in which R denotes an alkyl of $C_{1-12}$,

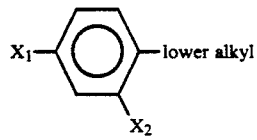

wherein $X_1$ and $X_2$ are same or different and are hydrogen or halogen, cyclohexylmethyl, cyclohexyl, tetrahydro-2H-pyran-l-yl methyl, carboxy-lower alkyl or chloro-lower alkyl and n is 2 or 3.

The invention also provides a process for the production of compounds of formula (I) or pharmaceutically acceptable salts thereof.

Finally, the present invention provides new aldose reductase inhibitors containing, as the effective component, a compound of formula (I) or a pharmaceutically acceptable salt thereof.

Among the compounds represented by formula (I), especially preferred are those in which R is benzyl, phenethyl, 2-fluoro-4-bromo-benzyl, cyclohexylmethyl, cyclohexyl, tetrahydro-2H-pyran-2-yl-methyl, alkyl of $C_{1-12}$ such as methyl, ethyl, propyl, isopropyl, butyl, isobutyl, t-butyl, pentyl, isopentyl, hexyl, heptyl, octyl, nonyl, decyl or undecyl, carboxy-lower alkyl such as carboxymethyl, 2-carboxyethyl, 3carboxypropyl or 4-carboxypropyl, chloro-lower alkyl such as chloromethyl, 2-chloroethyl, 3-chloropropyl or 4-chlorobutyl.

These novel compounds can be produced in accordance with the following reaction scheme:

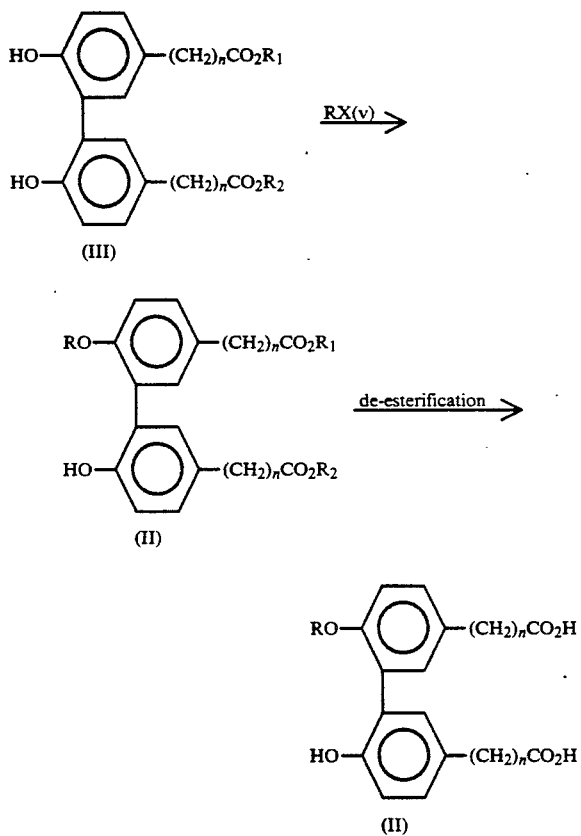

in which R and n have the meanings as given above, $R_1$ and $R_2$ are the same or different and represent radicals removable by hydrolysis and X denotes a halogen atom, by alkylating the compound of formula (III) using an alkyl halide of formula (V) to produce the compound of formula (II) and then splitting the ester group of formula (II) into a free acid of formula (I).

DETAILED DESCRIPTION OF THE INVENTION

As the alkyl halide of formula (V) used for alkylating the esterified compound of formula (III), there may be exemplified benzyl bromide, phenethyl bromide, 2-fluoro-4-bromo-benzyl bromide, cyclohexylmethyl bromide, cyclohexyl bromide, tetrahydro-2H-pyran-2-yl methyl bromide, alkyl bromide of $C_{1-12}$, bromo-lower fatty acid ethyl ester or ω-bromo-lower alkyl chloride.

The alkylation can be performed in an organic solvent which will not participate in the reaction, such as DMF, acetone, dioxane, tetrahydrofuran, benzene, toluene, xylene, ethyl acetate, methanol, ethanol or so on, by introducing therein the esterified compound (III) and the alkyl halide (V) and conducting the reaction in the presence of an inorganic or organic base, for example, an alkali metal carbonate such as anhydrous potassium carbonate or anhydrous sodium carbonate; an alkali metal hydroxide such as sodium or potassium hydroxide; a tertiary alkylamine such as trimethylamine or triethylamine; pyridine, or a pyridine derivative such as picoline, lutidine or 4-dimethylaminopyridine; a diazabicyclo compound such as 1,5-diazabicyclo (4.3.0)-nonene-5,1,4-diazabicyclo (2.2.2)-octane, 1,8-diazabicyclo (5.4.0)-undecene-7; or a metal alkoxide such as sodium methoxide or sodium ethoxide, together with, if necessary, a small amount of copper powder as catalyst.

The reaction is carried out in general at room temperature, or under heating to 50°–100° C. for poorly reactive compounds, for 1 to 50 hours with stirring. The amount of the reagents and catalyst may preferably be in the range from 1 to 20 moles of the halide, from 1.2 to 1.3 moles of the base and from 0.5 to 1.5 times by weight of the catalyst per mole of the starting compound.

Among the starting compounds, namely, the esterified biphenyl compounds of formula (III), the compound in which n is 2 is known (Tetrahedron Letters, 52; 5211 (1978)) and the compound in which n is 3 (IIIb) can be prepared easily as shown in the following reaction scheme:

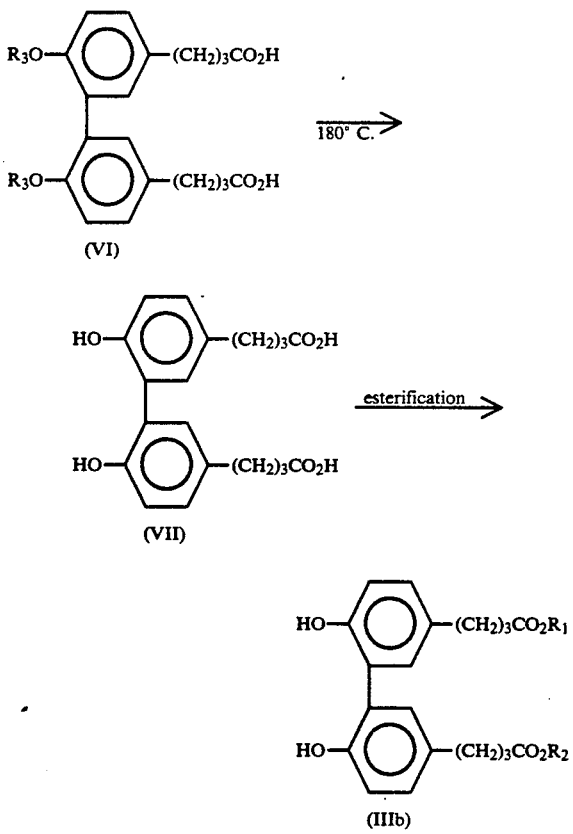

by reacting pyridine-hydrochloric acid with a compound of formula (VI) at about 180° C. to convert the alkoxy group into hydroxy, and then esterifying the carboxyl groups of the resulting product of formula (VII) with a lower alcohol or the like.

The de-esterification reaction, namely, hydrolysis of the ester groups of the resulting compound of formula (II), can be effected by reacting the ester in an organic solvent such as ethanol, methanol, dioxane, tetrahydrofuran or acetonitrile, with a base such as sodium hydroxide or potassium hydroxide for 4 hours to 1–3 days at room temperature with stirring. The concentration of the base to be employed may in general be in the range from 1 to 3N and it is preferable to use it in an amount of about 2–10 moles per mole of the compound of formula (II).

The compound of formula (I) according to the present invention obtained as above can further be purified as required using any known purifying technique such as column chromatography on silica gel, recrystallization and so on.

A compound of formula (I) according to the present invention can be converted into a corresponding pharmaceutically acceptable salt of an inorganic cation of, for example, an alkali metal such as sodium or potassium; an alkaline earth metal such as calcium or magnesium; and ammonium, or of an organic cation of, for example, a non-toxic organic amine.

For preparing an inorganic salt, the compound of formula (I) according to the present invention is preferably dissolved first in an aqueous solution containing at least an equivalent amount of hydroxide, carbonate or bicarbonate of a metal corresponding to the contemplated inorganic salt. For such salt formation by reaction with a metal compound, a watermiscible organic solvent inert to the reaction, such as methanol, ethanol, acetone or dioxane may be admixed with the reaction mixture. If sodium hydroxide, sodium carbonate or sodium bicarbonate is employed, a solution of the corresponding sodium salt will be obtained.

A solid salt can be obtained by evaporating the solvent of such solution or by adding to the solution a water-soluble organic solvent having some polarity, such as butanol, ethyl methyl ketone or so on, to cause deposition of the solid salt.

The compounds of formula (I) according to the present invention or the pharmaceutically acceptable salts thereof can be administered to humans as an aldose reductase inhibitor as such or in the form of a preparation with a known carrier substance.

The aldose reductase inhibitor according to the present invention can be administered to human patients or to experimental animals, for example, orally, rectally or parenterally, such as, by intravenous, intramuscular, subcutaneous, intraperitoneal and ophthalmic administration. The preparation of the compound according to the present invention may be formulated so as to adapt to each of the above administration means.

The preparation may be in any conventional form for human administration, such as pellets, pills, powders, granules, capsules, suppositories, injectables, eye drops, etc. For formulating such preparations for oral administration, such as tablets, granules and capsules, the compound according to the present invention may be mixed with excipients serving as carrier substances, for example starch, lactose, sucrose, mannite, carboxymethyl cellulose, corn starch and various inorganic salts; binders, such as starch, dextrin, gum arabic, gelatin, hydroxypropyl starch, methyl cellulose, sodium carboxymethyl cellulose, hydroxypropyl cellulose, crystalline cellulose, ethyl cellulose, polyvinyl pyrrolidone and macrogol; disintegrators, such as starch, hydroxypropyl starch, carboxymethyl cellulose, sodium carboxymethyl cellulose and hydroxypropyl cellulose; surface active agents, such as sodium lauryl sulfate, soybean lecithin, fatty acid esters of sucrose and polysorbate 80; lubricating agents, such as talc, wax, hydrogenated vegetable oil, fatty acid esters of sucrose, magnesium stearate and calcium stearate; fluidizing agents; coloring agents, flavors and so on.

The compounds of formula (I) according to the present invention or pharmaceutically acceptable salts thereof can be administered in a form of suspensions, emulsions, syrups or elixirs.

For parenteral preparations, there may be used distilled water for injection, physiological saline solutions, aqueous solutions of glucose, vegetable oils for injection, propylene glycol, polyethylene glycol and so on as the diluent. It is permissible to further incorporate as required sterilizers, antiseptics, stabilizers and so on. It is possible to prepare such parenteral preparations in consideration of their low stability, as freeze-dried products by after filling into a suitable vessel, such as glass vial, freeze drying so as to permit reproducing the preparation directly before its use by diluting with an appropriate diluent. It is also possible to incorporate into the preparation as required tonicity agents, stabilizers, aseptics, analgesics and so on.

The amount of administration of the compound of formula (I) or the pharmaceutically acceptable salt thereof according to the present invention may vary in accordance with each selected administration route and with the condition of the recipient such as age, body weight, disease condition and so on. It may be in general in the range from 5 milligrams to 1 gram, preferably in the range from about 25 milligrams to about 300 milligrams, calculated as the compound of formula (I), as the total amount per day for an adult human. The frequency of administration may be up to three times a day.

Various compounds of formula (I) according to the present invention have been examined for their pharmacodynamic behavior and for their acute toxicity, of which the results are given below.

1) Method for Determining the Inhibitory Activity on Enzyme Reaction

The preparation of aldose reductase and the determination of its inhibitory action on enzyme reaction activity were carried out pursuant to the procedures disclosed by Haymann et al. in *Journal of Biological Chemistry*, 240, 877 (1965).

The sample solution to be examined for inhibitory activity was prepared by dissolving a compound of formula (I) according to the present invention in a small amount of methanol and increasing the volume of the resulting methanol solution by diluting it with distilled water up to tenfold volume. A partially purified bovine lens aldose reductase was used for the assay.

To 2.4 ml of a solution of $5 \times 10^{-5}$ M NADPH dissolved in a 2/15M phosphate buffer solution (pH 6.0), 0.4 ml of the enzyme solution (15 m units/ml) and 0.1 ml of the sample solution to be examined were added and the mixture was introduced into a quartz cell in a photoelectric photometer and subjected to pre-incubation at 37° C. for 4 mins. Then, 0.1 ml of a 0.015M D,L-glyceraldehyde solution was added thereto for initiating the enzyme reaction and the decrease in the optical absorption at 340 nm was measured at 37° C. for 4 mins.

The inhibitory activity on aldose reductase was calculated by the following equation:

$$\frac{B-A}{B} \times 100 \, (\%)$$

in which A represents the enzyme reaction rate with addition of the inhibitor and B denotes the enzyme reaction rate without addition of the inhibitor.

2) Activity for Suppressing Accumulation of Sorbitol (A) Tissue Culture

Lenses and sciatic nerves extirpated from Wistar rats, male, aged 7 weeks, were washed twice with an aseptic buffer solution consisting of 0.3% trisaminomethane, 0.8% NaCl, 0.038% KCl, 0.025% $Na_2HPO_4 \cdot 12H_2O$, 0.1% glucose and 1.85 ml/l of concentrated HCl.

The lenses and the sciatic nerves were then preincubated for 30 mins. in a culture medium prepared by adding 2 ml of 7.5% $NaHCO_3$ aseptic solution and 5.5 ml of aseptic calf fetus serum to 100 ml of an aseptic culture medium of 0.98% TC Medium 199 (NISSUI Corp.) containing 0.01% of dihydrostreptomycin and 0.01% of benzylpenicillin. Thereafter, the intrinsic culture was effected in a culture medium prepared by adding each sample solution to be examined and 0.9% of glucose to the abovementioned culture medium and permitting culturing to proceed for 20 hours. The incubation was effected at 37° C. in an atmosphere composed of 95% air and 5% $CO_2$.

After culturing, the cultured samples of lens and sciatic nerve were removed from the culture medium to filter paper and the weight of each of them was measured after the adherent culture solution had been blown off. Then, each of the cultured samples was homogenized with the addition of 1 ml of a cold 8% $HClO_4$ solution and the homogenized mixture was subjected to centrifugation at 10,000 G for 10 mins., whereby a supernatant was obtained. The resulting precipitate was then homogenized again with addition thereto of 0.5 ml of cold 8% $HClO_4$ solution and the homogenized mixture was again subjected to centrifugation in a similar way as above to obtain a further supernatant. This was combined with the previously obtained supernatant and the resulting solution was neutralized with 2N KOH aq. solution and was supplemented with distilled water to a volume of 5 ml. The precipitate formed by neutralization was separated by centrifugation at 3,000 rpm for 10 mins. and the resulting supernatant was employed as the sample for determining the sorbitol content.

(B) Determination of Sorbitol Content

The determination of the sorbitol content in the lens and in the sciatic nerve was carried out in accordance with the method of Bergmeyer in "*Methods of Enzymatic Analysis*" edited by H. U. Bergmeyer, pp 1323-1326, Academic Press, New York, 1974 and in accordance with the method of Malaon et al. in "*Diabetes*" 29, 861-864 (1980).

To 0.5 ml of the sample solution for determination of sorbitol content obtained as above, 0.9 ml of 0.1M glycine-KOH buffer solution (pH 9.4) containing 1 mM of $NAD^+$ and 0.1 ml of a solution of sorbitol dehydrogenase of 20 units/ml were added and the resulting mixture was subjected to incubation at 37° C. for 1 hour.

The content of sorbitol in each tissue was estimated by assuming the increment of the optical absorption at 340 nm to be proportional to the amount of NADH produced by the reaction for the lens and by detecting the fluorescence with an excitation wavelength of 366 nm and a fluorescence wavelength of 425 nm for the sciatic nerve.

The activity for suppressing accumulation of sorbitol, i.e. the aldose reductase inhibiting activity, was calculated from the determined sorbitol content by the calculation formula $$\frac{(B - C) - (A - C)}{(B - C)} \times 100 \, (\%)$$

in which A denotes the content of sorbitol per unit weight of the tissue after cultivation with addition of the inhibitor, B denotes the sorbitol content per unit weight of the tissue after cultivation without addition of the inhibitor and C represents the sorbitol content per unit weight of the tissue after cultivation in the medium without addition of glucose and inhibitor.

The results of the tests according to 1) and 2) above are summarized in Table 1 below. Here, it is to be pointed out that the diester intermediate of formula (II) in the production of the compound of formula (I) according to the present invention, for example the compounds obtained in Reference Examples 1-15, 16, 17 and 21-31 given afterwards, did not exhibit any aldose reductase inhibiting activity, i.e. no activity for suppressing accumulation of sorbitol.

TABLE 1

| Example No. | Concentration (μg/ml) | Enzyme Reaction Inhibitory Activity (%) | Inhibition of sorbitol Accumulation (%) | |
|---|---|---|---|---|
| | | | Lens | Sciatic Nerve |
| 1 | 5 | | 69.9 | |
| | 1.0 | 92.8 | | 64.6 |
| | 0.1 | 60.8 | | |
| 2 | 1.0 | 89.1 | | |
| | 0.1 | 54.0 | | |
| 3 | 5 | | 85.2 | |
| | 2.5 | 44.7 | | |
| | 1.0 | 91.9 | | 73.2 |
| | 1.0 | | | 64.8 |
| | 0.1 | 73.6 | | |
| 4 | 1.0 | 88.2 | | |
| | 0.1 | 50.4 | | |
| 5 | 5 | | 79.2 | |
| | 2.5 | 32.7 | | |
| | 1.0 | 90.0 | | 73.3 |
| | 1.0 | | | 73.8 |
| | 0.1 | 73.6 | | |
| 6 | 1.0 | 90.0 | | |
| | 0.1 | 58.6 | | |
| 7 | 1.0 | 90.9 | | |
| | 0.1 | 56.4 | | |
| 8 | 1.0 | 91.9 | | |
| | 0.1 | 58.6 | | |
| 9 | 5 | | 65.0 | |
| | 1.0 | 91.9 | | 37.8 |
| | 0.1 | 65.3 | | |
| 10 | 5 | | 37.7 | |
| | 1.0 | 93.7 | | 33.6 |
| | 0.1 | 67.4 | | |
| 11 | 1.0 | 92.8 | | 34.7 |
| | 0.1 | 81.5 | | |
| 12 | 5 | | 78.1 | |
| | 1.0 | 89.1 | | 59.5 |
| | 0.1 | 61.9 | | |
| 13 | 1.0 | 95.2 | | |
| | 0.1 | 60.6 | | |
| 14 | 1.0 | 90.5 | | 62.4 |
| | 0.1 | 52.4 | | |
| 15 | 1.0 | 89.6 | | 43.2 |
| | 0.1 | 47.6 | | |
| 16 | 2.5 | | 59.3 | |
| | 1.0 | | | 47.7 |
| | 0.1 | 51.4 | | |
| 17 | 0.02 | 21.1 | | |
| | 2.5 | | 47.2 | |
| | 1.0 | | | 69.2 |
| | 0.1 | 55.0 | | |
| | 0.02 | 19.5 | | |
| 18 | 0.1 | 60.6 | | |
| | 0.02 | 22.0 | | |
| 19 | 0.1 | 62.6 | | |
| | 0.02 | 23.8 | | |
| 20 | 1.0 | | | 51.5 |
| | 0.1 | 73.1 | | |
| | 0.02 | 18.7 | | |
| 21 | 2.5 | | 48.8 | |
| | 1.0 | | | 75.4 |
| | 0.1 | 52.7 | | |
| | 0.02 | 14.7 | | |
| 22 | 0.1 | 63.9 | | |
| | 0.02 | 27.2 | | |
| 23 | 2.5 | | 55.3 | |
| | 1.0 | | | 81.1 |
| | 0.1 | 69.2 | | |
| | 0.02 | 33.6 | | |
| 24 | 0.1 | 62.6 | | |
| | 0.02 | 25.6 | | |
| 25 | 0.1 | 69.2 | | |
| | 0.02 | 20.5 | | |
| 26 | 1.0 | | | 43.3 |
| | 0.1 | 73.1 | | |
| | 0.02 | 35.3 | | |
| 27 | 0.1 | 61.2 | | |
| | 0.02 | 23.8 | | |
| 28 | 1.0 | | | 69.0 |
| | 0.1 | 71.7 | | |
| | 0.02 | 28.8 | | |

3) Acute Toxicity

Compounds of formula (I) according to the present invention, as given in the examples below, were suspended in distilled water and were dissolved completely by adding at least the equimolar amount of aqueous NaOH solution. The pH of the resulting solutions was adjusted to 6.5-7.0 and the solutions were administered to STD-DDY mice, aged 5 weeks, 3 mice in a group, orally, 400 mg/20 ml/kg and each group was observed for 10 days. No death was observed in any of the administered groups.

As is clear from the experimental results, the compounds according to the present invention exhibit a superior inhibitory activity on aldose reductase and excellent stability, so that they can be used advantageously as aldose reductase inhibitors, for the prevention or therapy of cataracts, retinal diseases, noirosis, nephropathy, corneal disorders, diabetic uveitis and so on.

PREFERRED EMBODIMENTS OF THE INVENTION

Below, the present invention will further be described in more detail by way of concrete Examples and several Reference Examples.

REFERENCE EXAMPLE 1

Synthesis of 2-benzyloxy-2'-hydroxy-5,5'-bis (2-ethoxycarbonylethyl) biphenyl

To 1 ml of a DMF solution containing 55.5 mg (0.1438 mmol) of 2,2'-dihydroxy-5,5'-bis (2-ethoxycarbonylethyl) biphenyl and 21.82 μl (0.1798 mmol) of benzyl iodide, there was added 27.43 μl (0.1798 mmol) of DBU and the resulting mixture was agitated for 4.5 hours at room temperature. After the solvent in the reaction mixture was evaporated off under reduced pressure, the evaporated residue was dissolved in chloroform. This solution was washed with dilute hydrochloric acid, water and aqueous sodium chloride solution in this sequence and was dried by adding anhydrous sodium sulfate. The residue obtained after the solvent had been evaporated off was purified by silica gel column chromatography (with 5 g of WAKO-gel C-200, eluent: toluene and toluene/ethyl acetate of 50/1) to obtain 52.8 mg (0.111 mmol, 77%) of 2-benzyloxy-2'-hydroxy-5,5'-bis (2-ethyoxycarbonylethyl) biphenyl as an oily product. $^1$H-NMR (CDCl$_3$) δ (ppm): 1.23 (6H, t, 2CH$_3$), 2.5–2.8 (4H, m, 2CH$_2$), 2.8–3.1 (4H, m, 2CH$_2$), 4.13 (4H, q, 2CH$_2$), 5.06 (2H, s, CH$_2$), 6.27 (1H, s, OH), 6.8–7.4 (11H, m, arom-H) MS (FAB): 475 (M-H)$^-$

REFERENCE EXAMPLE 2

Synthesis of (2-fluoro-4-bromobenzyloxy)-2'-hydroxy-5, 5'-bis (2-ethoxycarbonylethyl) biphenyl To 5 ml of a DMF solution containing 200 mg (0.5181 mmol) of 2,2'-dihydroxy-5,5'-bis (2-ethoxycarbonylethyl) biphenyl and 716.7 μl (5.181 mmol) of 2-fluoro-4-bromobenzylbromide, there was added 85.8 mg (0.6217 mmol) of anhydrous potassium carbonate and a small amount of copper powder and the resulting mixture was agitated for 1 hour at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, water and aequeous sodium bicarbonate, water and aqueous sodium cholride solution in this sequene and was dried by adding anhydrous sodium sulfate. The residue obtained after the solvent had been evaporated off was purified by silica gel column chromatography (with 50 g of WAKO-gel C-200, eluent: toluene and toluene/ethyl acetate of 100/1 and 50/1) to obtain 212.4 mg (0.3706 mmol, 72%) of 2-(2-fluoro-4-bromobenzyloxy)-2'-hydroxy-5,5'-bis (2-ethoxycarbonylethyl) biphenyl as an oily product.

$^1$H-NMR (CDCl$_3$) δ (ppm): 1.23 (6H, t, 2CH$_3$), 2.5–2.8 (4H, m, 2CH$_2$), 2.8–3.1 (4H, m, 2CH$_2$), 4.13 (4H, q, 2CH$_2$), 5.05 (2H, s, CH$_2$), 5.95 (1H, s, OH), 6.8–7.3 (9H, m, arom-H) MS (FAB): 571 (M-H)$^-$

REFERENCE EXAMPLE 3

Synthesis of 2-cyclohexylmethoxy-2'-hydroxy-5,5'-bis (2-ethoxycarbonylethyl) biphenyl To 3 ml of a DMF solution containing 100 mg (0.259 mmol) of 2,2'-dihydroxy-5,5'-bis (2-ethoxycarbonylethyl) biphenyl and 365.2 μl (2.591 mmol) of cyclohexylmethyl bromide, there were added 42.9 mg (0.3109 mmol) of anhydrous potassium carbonate and a small amount of copper powder and the resulting mixture was agitated for 36 hours at room temperature. After 22 hours from the start of the reaction, 365.2 μl (2.591 mmol) of cyclohexylmethyl bromide was further added thereto. The reaction mixture was filtered by suction through Celite to remove the solid matter and the filtrate was washed with ethyl acetate. After the solvent in the filtrate was evaporated off under reduced pressure, the residue was dissolved in chloroform. This solution was washed with dilute hydrochloric acid, dilute aqueous sodium bicarbonate, water and sodium chloride aqueous solution in this sequence and was dried by adding anhydrous sodium sulfate. The residue obtained after the solvent had been evaporated off was purified by silica gel column chromatography (with 10 g of WAKO-gel C-200, eluent: hexane and toluene/ethyl acetate of 100/1 and 25/1) to obtain 105.2 mg (0.2486 mmol, 84%) of 2-cyclohexylmethoxy-2'-bis (2-ethoxycarbonylethyl) biphenyl as an oily product.

$^1$H-NMR (CDCl$_3$) δ (ppm): 0.8–2.0 (11H, m, cyclohexyl-H), 1.23 (6H, t, 2CH$_3$), 2.5–2.8 (4H, m, 2CH$_2$), 2.8–3.1 (4H, m, 2CH$_2$), 3.81 (2H, d, CH$_2$), 4.13 (4H, q, 2CH$_2$), 6.50 (1H, s, OH), 6.8–7.3 (6H, m, arom-H) MS (FAB): 481 (M-H)$^-$

REFERENCE EXAMPLE 4

Synthesis of 2-(tetrahydro-2H-pyran-2-yl) methoxy-2'-hydroxy-5,5'-bis (2-ethoxycarbonylethyl) biphenyl To 5 ml of a DMF solution containing 200 mg (0.5181 mmol) of 2,2'-dihydroxy-5,5'-bis (2-ethoxycarbonylethyl) biphenyl and 678 μl (5.181 mmol) of 2-bromomethyl-tetrahydro-2H-pyran, there were added 85.8 mg (0.6217 mmol) of anhydrous potassium carbonate and a small amount of copper powder and the resulting mixture was agitated for 1 hour at 100° C. The reaction mixture was filtered by suction through Celite to remove the solid matter and the filtrate was washed with ethyl acetate. After the solvent in the filtrate was evaporated off under reduced pressure, the residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel column chromatography (with 10 g of WAKO-gel C-200, eluent: hexane and toluene/ethyl acetate of 100/1 and 50/1 and 30/1) to obtain 134.5 mg (0.2779 mmol, 54%) of 2-tetrahydro-2H-pyran-2-yl) methoxy-2'-hydroxy-5,5'-bis (2-ethoxy-carbonylethyl) biphenyl as an oily product.

$^1$H-NMR (CDCl$_3$) δ (ppm): 1.1–2.0 (6H, m, 3CH$_2$), 1.24 (6H, t, 2CH$_3$), 2.5–2.8 (4H, m, 2CH$_2$), 2.8–3.1 (4H, m, 2CH$_2$), 3.2–3.8 (2H, m, CH$_2$), 3.8–4.3 (7H, m, 3CH$_2$, CH), 6.72 (1H, s, OH), 6.8–7.3 (6H, m, arom-H) MS (FAB): 483 (M-H)$^-$

REFERENCE EXAMPLE 5

Synthesis of 2-propoxy-2'-hydroxy-5,5'-bis (2-ethoxycarbonylethyl) biphenyl

To 5 ml of a DMF solution containing 200 mg (0.5181 mmol) of 2,2'-dihydroxy-5,5'-bis (2-ethoxycarbonylethyl) biphenyl and 475.4 μl (5.181 mmol) of propyl bromide, there were added 85.8 mg (0.6217 mmol) of anhydrous potassium carbonate and a small amount of copper powder and the resulting mixture was agitated for 17 hours at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel column chromatography (with 10 g of WAKO-gel C-200, eluent: hexane and toluene/ethyl acetate of 100/1 and 50/1) to obtain 188.3 mg (0.4399 mmol, 85%) of 2-propoxy-'2-hydroxy-5,5'-bis (2-ethoxycarbonylethyl) biphenyl as an oily product.

$^1$H-NMR (CDCl$_3$) δ (ppm): 0.93 (3H, t, CH$_3$), 1.23 (6H, t, 2CH$_3$), 1.5–2.0 (2H, m, CH$_2$), 2.5–2.8 (4H, m, 2CH$_2$), 2.8–3.1 (4H, m, 2CH$_2$), 3.98 (2H, t, CH$_2$), 4.13 (4H, q, 2CH$_2$), 6.57 (1H, s, OH), 6.8–7.3 (6H, m, arom-H) MS (FAB): 427 (M-H)$^-$

REFERENCE EXAMPLE 6

Synthesis of 2-butoxy-2'-hydroxy-5,5'-bis (2-ethyoxycarbonylethyl) biphenyl

To 3 ml of a DMF solution containing 100 mg (0.2591 mmol) of 2,2'-dihydroxy-5,5'-bis (2-ethoxycarbonylethyl) biphenyl and 281.1 μl (2.591 mmol) of butyl bromide, there were added 42.9 mg (0.3109 mmol) of anhydrous potassium carbonate and a small amount of copper powder and the resulting mixture was agitated for 23 hours at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel column chromatography (with 10 g of WAKO-gel C-200 eluent: hexane and toluene/ethyl acetate of 100/1 and 50/1) to obtain 99.6 mg (0.2253 mmol, 87%) of 2-butoxy-2'-hydroxy-5,5'-bis (2ethoxycarbonylethyl) biphenyl as an oily product.

$^1$H-NMR (CDCl$_3$) δ (ppm): 0.88 (3H, t, CH$_3$), 1.23 (6H, t, 2CH$_3$), 1:20–2.0 (4H, m, 2CH$_2$), 2.5–2.8 (4H, m, 2CH$_2$), 2.8–3.1 (4H, m, 2CH$_2$), 4.02 (2H, t, CH$_2$), 4.13 (4H, q, 2CH$_2$), 6.56 (1H, s, OH), 6.8–7.3 (6H, m, arom-H) MS (FAB): 441 (M-H)$^-$

REFERENCE EXAMPLE 7

Synthesis of 2-pentyloxy-2'-hydroxy-5,5'-bis (2ethoxycarbonylethyl) biphenyl

To 5 ml of a DMF solution containing 100 mg (0.2591 mmol) of 2,2'-dihydroxy-5,5'-bis (2-ethoxycarbonylethyl) biphenyl and 331.3 μl (2.591 mmol) of pentyl bromide, there were added 42.9 mg (0.3109 mmol) of anhydrous potassium carbonate and a small amount of copper powder and the resulting mixture was agitated overnight at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel column chromatography (with 7 g of WAKO-gel C-200, eluent: hexane and toluene/ethyl acetate of 50/1) to obtain 97.2 mg (0.2131 mmol, 82%) of 2-pentyloxy-2'-hydroxy-5,5'-bis (2ethoxycarbonylethyl) biphenyl as an oily product.

$^1$H-NMR (CDCl$_3$) δ (ppm): 0.85 (3H, t, CH$_3$), 1.23 (6H, t, 2CH$_3$), 1.1–1.5 (4H, m, 2CH$_2$), 1.6–1.9 (2H, m, CH$_2$), 2.5–2.8 (4H, m, 2CH$_2$), 2.8–3.1 (4H, m, 2CH$_2$), 4.01 (2H, t, CH$_2$), 4.13 (4H, q, 2CH$_2$), 6.57 (1H, s, OH), 6.8–7.3 (6H, m, arom-H) MS (FAB): 455 (M-H)$^-$

REFERENCE EXAMPLE 8

Synthesis of 2-hexyloxy-2'-hydroxy-5,5'-bis (2-ethoxycarbonylethyl) biphenyl

To 4 ml of a DMF solution containing 97 mg (0.2513 mmol) of 2,2'-dihydroxy-5,5'-bis (2-ethoxycarbonylethyl) biphenyl and 363.7 μl (2.513 mmol) of hexyl bromide, there were added 41.6 mg (0.3109 mmol) of anhydrous potassium carbonate and a small amount of copper powder and the resulting mixture was agitated overnight at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel column chromatography (with 10 g of WAKO-gel C-200, eluent: hexane and toluene/ethyl acetate of 100/1) to obtain 94.4 mg (0.2008 mmol, 80%) of 2-hexyloxy-2'-hydroxy-5,5'-bis (2ethoxycarbonylethyl) biphenyl as an oily product.

$^1$H-NMR (CDCl$_3$) δ (ppm): 0.83 (3H, t, CH$_3$), 1.23 (6H, t, 2CH$_3$), 1.1–1.5 (6H, m, 3CH$_2$), 1.6–1.9 (2H, m, CH$_2$), 2.5–2.8 (4H, m, 2CH$_2$), 2.8–3.1 (4H, m, 2CH$_2$), 4.01 (2H, t, CH$_2$), 4.13 (4H, q, 2CH$_2$), 6.57 (1H, s, OH), 6.8–7.3 (6H, m, arom-H) MS (FAB): 469 (M-H)$^-$

REFERENCE EXAMPLE 9

Synthesis of 2-heptyloxy-2'-hydroxy-5,5'-bis (2-ethoxy-carbonylethyl) biphenyl

To 4 ml of a DMF solution containing 94 mg (0.2435 mmol) of 2,2'-dihydroxy-5,5'-bis (2-ethoxycarbonylethyl) biphenyl and 394.4 μl (2.435 mmol) of heptyl bromide, there were added 40.3 mg (0.3109 mmol) of anhydrous potassium carbonate and a small amount of copper powder and the resulting mixture was agitated overnight at room temperature. The reaction mixture was filtered by suction through elite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel column chromatography (with 10 g of WAKO-gel C-200, eluent: benzene and benzene/ethyl acetate of 300/1, 150/1 and 50/1) to obtain 88.1 mg (0.182 mmol, 75%) of 2-heptyloxy-2'-hydroxy-5,5'-bis (2-ethoxycarbonylethyl) biphenyl as an oily product. $^1$H-NMR (CDCl$_3$) δ (ppm): 0.85 (3H, t, CH$_3$), 1.23 (6H, t, 2CH$_3$), 1.1–1.5 (8H, m, 4CH$_2$), 1.6–1.9 (2H, m, CH$_2$), 2.5–2.8 (4H, m, 2CH$_2$), 2.8–3.1 (4H, m, 2CH$_2$), 4.01 (2H, t, CH$_2$), 4.13 (4H, q, 2CH$_2$), 6.58 (1H, s, OH), 6.8–7.3 (6H, m, arom-H) MS (FAB): 483 (M-H)$^-$

REFERENCE EXAMPLE 10

Synthesis of 2-octyloxy-2'-hydroxy-5,5'-bis (2-ethoxycarbonylethyl) biphenyl

To 5 ml of a DMF solution containing 200 mg (0.5181 mmol) of 2,2'-dihydroxy-5,5'-bis (2-ethoxycarbonylethyl) biphenyl and 913.3 μl (5.181 mmol) of octyl bromide, there were added 85.5 mg (0.6217 mmol) of anhydrous potassium carbonate and a small amount of copper powder and the resulting mixture was agitated overnight at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel column chromatography (with 20 g of WAKO-gel C-200, eluent: toluene and toluene/ethyl acetate of 100/1 and 50/1) to obtain 230.4 mg (0.627 mmol, 89%) of 2-octyloxy-2'-hydroxy-5,5'-bis (2-ethoxycarbonylethyl) biphenyl as an oily product.

$^1$H-NMR (CDCl$_3$) δ (ppm): 0.87 (3H, t, CH$_3$), 1.24 (6H, t, 2CH$_3$), 1.1–1.5 (10H, m, 5CH$_2$), 1.5–1.9 (2H, m, CH$_2$), 2.5–2.8 (4H, m, 2CH$_2$), 2.8–3.1 (4H, m, 2CH$_2$), 4.01 (2H, t, CH$_2$), 4.14 (4H, q, 2CH$_2$), 6.58 (1H, s, OH), 6.8–7.3 (6H, m, arom-H) MS (FAB): 497 (M-H)$^-$

REFERENCE EXAMPLE 11

Synthesis of 2-undecyloxy-2'-hydroxy-5,5'-bis (2-ethoxycarbonylethyl) biphenyl

To 5 ml of a DMF solution containing 200 mg (0.5181 mmol) of 2,2'-dihydroxy-5,5'-bis (2-ethoxycarbonylethyl) biphenyl and 1179.8 μl (5.181 mmol) of undecyl bromide, there were added 85.8 mg (0.6217 mmol) of anhydrous potassium carbonate and a small amount of copper powder and the resulting mixture was agitated overnight at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel column chromatography (with 20 g of WAKO-gel C-200, eluent: toluene and toluene/ethyl acetate of 100/1) to obtain 245.5 mg (0.456 mmol, 88%) of 2-undecyloxy-2'-hydroxy-5,5'-bis (2-ethoxycarbonylethyl) biphenyl as an oily product.

$^1$H-NMR (CDCl$_3$) δ (ppm): 0.88 (3H, t, CH$_3$), 1.1–1.5 (22H, m, 8CH$_2$, 2CH$_3$), 1.6–1.9 (2H, m, CH$_2$), 2.5–2.8 (4H, m, 2CH$_2$), 2.8–3.1 (4H, m, 2CH$_2$), 4.01 (2H, t, CH$_2$), 4.13 (4H, q, 2CH$_2$), 6.58 (1H, s, OH), 6.8–7.3 (6H, m, arom-H) MS (FAB): 539 (M-H)$^-$

REFERENCE EXAMPLE 12

Synthesis of 2-isopentyloxy-2'-hydroxy-5,5'-bis (2ethoxycarbonylethyl) biphenyl

To 5 ml of a DMF solution containing 200 mg (0.5181 mmol) of 2,2'-dihydroxy-5,5'-bis (2-ethoxycarbonylethyl) biphenyl and 646.5 μl (5.181 mmol) of isopentyl bromide, there were added 85.8 mg (0.6217 mmol) of anhydrous potassium carbonate and a small amount of copper powder and the resulting mixture was agitated overnight at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel column chromatography (with 20 g of WAKO-gel C-200, eluent: toluene and toluene/ethyl acetate of 100/1 and 50/1) to obtain 8.2 mg (0.456 mmol, 88%) of 2-isopentyloxy-2'-hydroxy-5,5'-bis (2-ethoxycarbonylethyl) biphenyl as an oily product.

$^1$H-NMR (CDCl$_3$) δ (ppm): 0.86 (6H, d, 2CH$_3$), 1.24 (6H, t, 2CH$_3$), 1.5–1.8 (3H, m, CH$_2$, CH), 2,5–2.8 (4H, m, 2CH$_2$), 2.8–3.1 (4H, m, 2CH$_2$), 4.04 (2H, t, CH$_2$), 4.13 (4H, q, 2CH$_2$), 6.55 (1H, s, OH), 6.8–7.3 (6H, m, arom-H) MS (FAB): 455 (M-H)$^-$

REFERENCE EXAMPLE 13

Synthesis of 2-(3-ethoxycarbonylpropoxy)-2'-hydroxy-5,5'-bis (2-ethoxycarbonylethyl) biphenyl To 5 ml of a DMF solution containing 200 mg (0.5181 mmol) of 2,2'-dihydroxy-5,5'-bis (2-ethoxycarbonylethyl) biphenyl and 780.5 μl (5.181 mmol) of 4-bromobutylic acid ethyl ester, there were added 85.8 mg (0.6217 mmol) of anhydrous potassium carbonate and a small amount of copper powder and the resulting mixture was agitated overnight at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel column chromatography (with 20 g of WAKO-gel C-200, eluent: toluene and toluene-/ethyl acetate of 50/1, 30/1, 20/1, 10/1, 9/1 and 8/1) to obtain 100.7 mg (0.2014 mmol, 39%) of 2-(3-ethoxycarbonylpropoxy)-2'-hydroxy-5,5'-bis(2-ethoxycarbonylethyl) biphenyl as an oily product.

$^1$H-NMR (CDCl$_3$) δ (ppm): 1.22 (3H, t, CH$_3$), 1.23 (6H, t, 2CH$_3$), 1.8–2.2 (2H, m, CH$_2$), 2.2–2.5 (2H, m, CH$_2$), 2.5–2.8 (4H, m, 2CH$_2$), 2.8–3.1 (4H, m, 2CH$_2$), 3.9–4.3 (8H, m, 4CH$_2$), 6.24 (1H, s, OH), 6.8–7.3 (6H, m, arom-H) MS (FAB): 499 (M-H)$^-$

REFERENCE EXAMPLE 14

Synthesis of 2-phenethyloxy-2'-hydroxy-5,5'-bis (2-ethoxycarbonylethyl) biphenyl To 5 ml of a DMF solution containing 200 mg (0.5181 mmol) of 2,2'-dihydroxy-5,5'-bis (2-ethoxycarbonylethyl) biphenyl and 707.6 µl (5.181 mmol) of phenethyl bromide, there were added 85.8 mg (0.6217 mmol) of anhydrous potassium carbonate and a small amount of copper powder and the resulting mixture was agitated overnight at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel column chromatography (with 20 g of WAKO-gel C-200, eluent: toluene and toluene/ethyl acetate of 100/1 and 50/1 to obtain 218.1 mg (0.4451 mmol, 86%) of 2-phenethyloxy-2'-hydroxy-5,5'-bis (2-ethoxy-carbonylethyl) biphenyl as an oily product.

$^1$H-NMR (CDCl$_3$) δ (ppm): 1.23 (6H, t, 2CH$_3$), 2.5–2.8 (4H, m, 2CH$_2$), 2.8–3.1 (6H, m, 3CH$_2$), 4.12 (2H, q, CH$_2$). 4.13 (2H, q, CH$_2$), 4.2 0 (2H, t, CH$_2$), 6.20 (1H, s, OH), 6.8–7.3 (11H, m, arom-H) MS (FAB): 489 (M-H)$^-$

REFERENCE EXAMPLE 15

Synthesis of 2-cyclohexyloxy-5,5'-bis (2-ethoxycarbonylethyl) biphenyl

To 5 ml of a DMF solution containing 200 mg (0.5181 mmol) of 2,2'-dihydroxy-5,5'-bis (2-ethoxycarbonylethyl) biphenyl and 644.5 µl (5.181 mmol) of cyclohexyl bromide, there were added 85.8 mg (0.6217 mmol) of anhydrous potassium carbonate and a small amount of copper powder and the resulting mixture was agitated for 41 hours at room temperature, for a further 5 hours at 70° C. and for 8 hours at 100° C. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel column chromatography (with 20 g of WAKO-gel C-200, eluent: toluene and toluene/ethyl acetate of 1000/1 and 500/1) and further purified by silica-gel column chromatography (with 15 g of WAKO-gel C-200, eluent: hexane and hexane/ethyl acetate 50/1, 30/1, 15/1 and 12/1) to obtain 28.3 mg (0.0605 mmol, 12%) of 2-cyclohexyloxy-2'-hydroxy-5,5'-bis (2-ethoxycarbonylethyl) biphenyl as an oily product.

$^1$H-NMR (CDCl$_3$) δ (ppm): 1.23 (6H, t, 2CH$_3$), 1.0–2.0 (10H, m, cyclohexyl-5CH$_2$), 2.5–2.8 (4H, m, CH$_2$), 2.8–3.1 (4H, m, 2CH$_2$), 4.13 (4H, q, 2CH$_2$), 4.0–4.6 (1H, m, cyclohexyl-CH), 6.8–7.3 (6H, m, arom-H) MS (FAB): 467 (M-H)$^-$

EXAMPLE 1

Synthesis of 2-benzyloxy-2'-hydroxy-5,5'-bis (2carboxyethyl) biphenyl

To 0.5 ml of an ethanol solution containing 110 mg (0.2311 mmol) of 2-benzyloxy-2'-hydroxy-5,5'-bis (2-ethoxycarbonylethyl) biphenyl obtained in Reference Example 1, 762.4 µl (0.7626 mmol) of 1 N sodium hydroxide solution was added and the mixture was agitated for 4 hours. The solvent of the reaction mixture was evaporated off under reduced pressure and, to the resulting evaporated residue, water was added. The solution was washed with ether and was then acidified using 1 N hydrochloric acid and then 0.1 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 73 mg (0.1738 mmol, 75%) of 2-benzyloxy-2'-hydroxy-5,5'-bis (2carbonylethyl) biphenyl was obtained as an oily product.

$^1$H-NMR (CDCl$_3$) δ (ppm): 2.5–2.8 (4H, m, 2CH$_2$), 2.8–3.1 (4H, m, 2CH$_2$), 5.10 (2H, s, CH$_2$), 6.8–7.3 (11H, m, arom-H) MS (FAB): 419 (M-H)$^-$

EXAMPLE 2

Synthesis of 2-(2-fluoro-4-bromobenzyloxy)-2'-hydroxy-5,5'-bis (2-carboxyethyl) biphenyl To 5.1 ml of an ethanol solution containing 182.5 mg (0.3186 mmol) of 2-(2-fluoro-4-bromobenzyloxy)-2'-hydroxy-5,5'bis (2-ethoxycarbonylethyl) biphenyl obtained in Reference Example 2, 1.27 ml (1.27 mmol) of 1N sodium hydroxide solution was added and the mixture was agitated at room temperature for 50 hours. After 40 hours from the start of the reaction, 1.27 ml (1.27 mmol) of 1N-sodium hydroxide solution was further added thereto and the mixture was stirred at room temperature for 50 hours. The solvent of the reaction mixture was evaporated off under reduced pressure and, to the resulting evaporated residue, water was added. The solution thus obtained was washed with ether and was then acidified using 1N hydrochloric acid and then 0.1N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 150.5 mg (0.2912 mmol, 91%) of 2-(2-fluoro-4-bromobenzyloxy)-2'-hydroxy-5,5'-bis (2-carboxyethyl) biphenyl was obtained as an oily product.

$^1$H-NMR (CDCl$_3$) δ (ppm): 2.5–2.8 (4H, m, 2CH$_2$), 2.8–3.1 (4H, m, 2CH$_2$), 5.00 (2H, s, CH$_2$), 6.8–7.3 (9H, m, arom-H) MS (FAB): 515 (M-H)$^-$

EXAMPLE 3

Synthesis of 2-cyclohexylmethoxy-2'-hydroxy-5,5'-bis (2-carboxyethyl) biphenyl To 3.1 ml of an ethanol solution containing 93.3 mg (0.1936 mmol) of 2-cyclohexylmethoxy-2'-hydroxy-5,5'-bis (2ethoxycarbonylethyl) biphenyl obtained in Reference Example 3, 0.744 ml (0.744 mmol) of 1N sodium hydroxide was added and the mixture was agitated at room temperature for 50 hours. After 40 hours from the start of the reaction, 0.744 ml (0.744 mmol) of 1N sodium hydroxide solution was further added thereto. The solvent of the reaction mixture was evaporated off under reduced pressure and, to the resulting evaporated residue, water was added. The solution obtained was washed with ether and was then acidified using 1N hydrochloric acid and then 0.1N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent 72.8 mg (0.1709 mmol, 88%) of 2-cyclohexylmethoxy-2'-hydroxy-5,5'-bis (2-carboxyethyl) biphenyl was obtained as an oily product.

$^1$H-NMR (CDCl$_3$) δ (ppm): 0.6–2.0 (11H, m, cyclohexyl-H), 2.4–2.7 (4H, m, 2CH$_2$), 2.7–3.0 (4H, m, 2CH$_2$), 3.73 (2H, d, 2CH$_2$), 6.7–7.2 (6H, m, arom-H) MS (FAB): 425 (M-H)$^-$

EXAMPLE 4

Synthesis of 2-(tetrahydro-2H-pyran-2-yl) methoxy-2'-hydroxy-5,5'-bis (2-carboxyethyl) biphenyl To 3.67 ml of an ethanol solution containing 91.8 mg (0.1836 mmol) of 2-(tetrahydro-2H-pyran-2-yl)methoxy-2'-hydroxy-5,5'-bis (2-ethoxycarbonylethyl) biphenyl obtained in Reference Example 4, 0.734 ml (0.734 mmol) of 1N sodium hydroxide was added and the mixture was agitated at room temperature for 28 hours. After 18 hours from the start of the reaction, 0.734 ml (0.734 mmol) of 1N sodium hydroxide solution was further added thereto. The solvent of the reaction mixture was evaporated off under reduced pressure and, to the resulting evaporated residue, water was added. The solution obtained was washed with ether and was then acidified using 1N hydrochloric acid and then 0.1N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 76.3 mg (0.1783 mmol, 97%) of 2-(tetrahydro-2H-yl)methoxy-2'-hydroxy-5,5'-bis (2-carboxyethyl) biphenyl was obtained as an oily product.

$^1$H-NMR (CDCl$_3$) δ (ppm): 1.1–2.0 (6H, m, 3CH$_2$), 2.5–2.8 (4H, m, 2CH$_2$), 2.8–3.1 (4H, m, 2CH$_2$), 3.2–3.8 (2H, m, CH$_2$), 3.9–4.2 (3H, m, CH$_2$, CH), 6.7–7.3 (6H, m, arom-H) MS (FAB): 427 (M-H)$^-$

EXAMPLE 5

Synthesis of 2-propoxy-2'-hydroxy-5,5'-bis (2carboxyethyl) biphenyl

To 2.79 ml of an ethanol solution containing 149.5 mg (0.3493 mmol) of 2-propoxy-2'-hydroxy-5, 5'-bis (2-ethoxycarbonylethyl) biphenyl obtained in Reference Example 5, 2.79 ml (2.79 mmol) of 1 N sodium hydroxide was added and the mixture was agitated at room temperature for 22 hours. The solvent of the reaction mixture was evaporated off under reduced pressure and, to the resulting evaporated residue, water was added. The solution obtained was washed with ether and was then acidified using 1 N hydrochloric acid and then 0.1 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 124.7 mg (0.3352 mmol, 96%) of 2-propoxy-2'-hydroxy-5,5'-bis (2carboxyethyl) biphenyl was obtained as an oily product. $^1$H-NMR (CDCl$_3$) δ (ppm): 0.94 (3H, t, CH$_3$), 1.76 (2H, m, CH$_2$), 2.5–2.8 (4H, m, 2CH$_2$), 2.8–3.1 (4H, m, 2CH$_2$), 4.00 (2H, t, CH$_2$), 6.8–7.3 (6H, m, arom-H) MS (FAB): 371 (M-H)$^-$

EXAMPLE 6

Synthesis of 2-butoxy-2'-hydroxy-5,5'-bis (2-carboxyethyl) biphenyl

To 3.1 ml of an ethanol solution containing 84.5 mg (0.1912 mmol) of 2-butoxy-2'-hydroxy-5, 5'-bis (2-ethoxycarbonylethyl) biphenyl obtained in Reference Example 67, 0.765 ml (0.765 mmol) of 1 N sodium hydroxide was added and the mixture was agitated at room temperature for 50 hours. After 40 hours from the start of the reaction, 0.765 ml (0.765 mmol) of 1 N sodium hydroxide solution was further added thereto. The solvent of the reaction mixture was evaporated off under reduced pressure and, to the resulting evaporated residue, water was added. The solution obtained was washed with ether and was then acidified using 1 N hydrochloric acid and then 0.1 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 70.1 mg (0.1816 mmol, 95%) of 2-butoxy-2'-hydroxy-5,5'bis (2-carboxyethyl) biphenyl was obtained as an oily product. $^1$H-NMR (CDCl$_3$) δ (ppm): 0.89 (3H, t, CH$_3$), 1.2–1.9 (4H, m, 2CH$_2$), 2.5–2.8 (4H, m, 2CH$_2$), 2.8–3.1 (4H, m, 2CH$_2$), 4.05 (2H, t, CH$_2$), 6.8–7.3 (6H, m, arom-H) MS (FAB): 385 (M-H)$^-$

EXAMPLE 7

Synthesis of 2-pentyloxy-2'-hydroxy-5,5'-bis (2carboxyethyl) biphenyl

To. 1.16 ml of an ethanol solution containing 88.2 mg (0.1934 mmol) of 2-pentyloxy-2'-hydroxy-5,5'-bis (2-ethoxycarbonylethyl) biphenyl obtained in Reference Example 7, 0.580 ml (0.580 mmol) of 1N sodium hydroxide was added and the mixture was agitated at room temperature for 10.5 hours. After 5.5 hours from the start of the reaction, 0.1934 ml (0.1934 mmol) of 1N sodium hydroxide solution and methanol (1.16 ml) were further added thereto, then the mixture was stirred for hours and further stirred for 3 hours at 60° C. The solvent of the reaction mixture was evaporated off under reduced pressure and, to the resulting evaporated residue, water was added. The solution obtained was washed with ether and was then acidified using 1N hydrochloric acid and then 0.1N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 71 mg (0.1775 mmol, 92%) of 2-pentyloxy-2'-hydroxy-5,5'-bis (2-carboxyethyl) biphenyl was obtained as an oily product.

$^1$H-NMR (CDCl$_3$) δ (ppm): 0.85 (3H, t, CH$_3$), 1.2–1.5 (4H, m, 2CH$_2$), 1.5–1.9 (2H, m, 2CH$_2$), 2.5–2.8 (4H, m, 2CH$_2$), 2.8–3.1 (4H, m, 2CH$_2$), 4.03 (2H, t, CH$_2$), 6.8–7.3 (6H, m, arom-H) MS (FAB): 399 (M-H)$^-$

EXAMPLE 8

Synthesis of 2-hexyloxy-2'-hydroxy-5,5'-bis (2carboxyethyl) biphenyl

To 1.01 ml of an ethanol solution containing 79.2 mg (0.1685 mmol) of 2-hexyloxy-2'-hydroxy-5,5'-bis (2-ethoxycarbonylethyl) biphenyl obtained in Reference Example 8, 0.506 ml (0.506 mmol) of 1 N sodium hydroxide were added and the mixture was agitated at room temperature for 20 hours. After 5.5 hours from the start of the reaction, 0.168 ml (0.168 mmol) of 1 N sodium hydroxide solution and methanol (1.01 ml) were further added thereto and the mixture was stirred for 14.5 hours. The solvent of the reaction mixture was evaporated off under reduced pressure and to the resulting evaporated residue, water was added. The solution obtained was washed with ether and was then acidified using 1N hydrochloric acid and then 0.1N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 67.6 mg (0.1633 mmol, 97%) of 2-hexyloxy-2'-hydroxy-5,5'-bis (2-carboxyethyl) biphenyl was obtained as an oily product.

$^1$H-NMR (CDCl$_3$) δ (ppm): 0.84 (3H, t, CH$_3$), 1.1–1.5 (6H, m, 3CH$_2$), 1.5–1.9 (2H, m, CH$_2$), 2.5–2.8 (4H, m, 2CH$_2$), 2.8–3.1 (4H, m, 2CH$_2$), 4.04 (2H, t, CH$_2$), 6.8–7.3 (6H, m, arom-H) MS (FAB): 413 (M-H)$^-$

EXAMPLE 9

Synthesis of 2-heptyloxy-2'-hydroxy-5,5'-bis (2-carboxyethyl) biphenyl

To 2.5 ml of a methanol solution containing 74.3 mg (0.1535 mmol) of 2-heptyloxy-2'-hydroxy-5, 5'-bis (2-ethoxycarbonylethyl) biphenyl obtained in Reference Example 9, 0.614 ml (0.614 mmol) of 1 N sodium hydroxide was added and the mixture was agitated at room temperature for 54 hours. After 44 hours from the start of the reaction, 0.614 ml (0.614 mmol) of 1 N sodium hydroxide solution was further added thereto and the mixture was stirred for 10 hours. The solvent of the reaction mixture was evaporated off under reduced pressure and, to the resulting evaporated residue, water was added. The solution obtained was washed with ether and was then acidified using 1 N hydrochloric acid and then 0.1 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 63.2 mg (0.1477 mmol, 96%) of 2-heptyloxy-2'-hydroxy-5,5'-bis (2-carboxyethyl) biphenyl was obtained as an oily product. $^1$H-NMR (CDCl$_3$) δ (ppm): 0.85 (3H, t, CH$_3$), 1.1–1.5 (8H, m, 4CH$_2$), 1.5–1.9 (2H, m, CH$_2$), 2.5–2.8 (4H, m, 2CH$_2$), 2.8–3.1 (4H, m, 2CH$_2$), 4.04 (2H, t, CH$_2$), 6.8–7.3 (6H, m, arom-H) MS (FAB): 427 (M-H)$^-$

EXAMPLE 10

Synthesis of 2-octyloxy-2'-hydroxy-5,5'-bis (2-carboxyethyl) biphenyl

To 3.17 ml of a methanol solution containing 197.1 mg (0.3597 mmol) of 2-octyloxy-2'-hydroxy-5, 5'-bis (2-ethoxycarbonylethyl) biphenyl obtained in Reference Example 10, 3.17 ml (3.17 mmol) of 1 N sodium hydroxide solution was added and the mixture was agitated at room temperature for 22.5 hours. The solvent of the reaction mixture was evaporated off under reduced pressure and, to the resulting evaporated residue, water was added. The solution obtained was washed with ether and was then acidified using 1 N hydrochloric acid and then 0.1 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 173.2 mg (0.3917 mmol, 99%) of 2-octyloxy-2'-hydroxy-5,5'-bis (2-carboxyethyl) biphenyl was obtained as a oily product. $^1$H-NMR (CDCl$_3$) δ (ppm): 0.86 (3H, t, CH$_3$), 1.1–1.5 (10H, m, 5CH$_2$), 1.5–1.9 (2H, m, CH$_2$), 2.5–2.8 (4H, m, 2CH$_2$), 2.8–3.1 (4H, m, 2CH$_2$), 4.03 (2H, t, CH$_2$), 6.8–7.3 (6H, m, arom-H) MS (FAB): 441 (M-H)$^-$

EXAMPLE 11

Synthesis of 2-undecyloxy-2'-hydroxy-5,5'-bis (2-carboxyethyl) biphenyl

To 3.24 ml of an ethanol solution containing 218.6 mg (0.4048 mmol) of 2-undecyloxy-2'-hydroxy-5, 5'-bis (2ethoxycarbonylethyl) biphenyl obtained in Reference Example 11, 3.24 ml (3.24 mmol) of 1 N sodium hydroxide solution was added and the mixture was agitated at room temperature for 22.5 hours. The solvent of the reaction mixture was evaporated off under reduced pressure and, to the resulting evaporated residue, water was added. The solution obtained was washed with ether and was then acidified using 1 N hydrochloric acid and then 0.1 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 191.9 mg (0.3965 mmol, 98%) of 2-undecyloxy-2'-hydroxy-5,5'-bis (2-carboxyethyl) biphenyl was obtained as an oily product. $^1$H-NMR (CDCl$_3$) δ (ppm): 0.88 (3H, t, CH$_3$), 1.1–1.5 (6H, m, 8CH$_2$), 1.5–1.9 (2H, m, CH$_2$), 2.5–2.8 (4H, m, 2CH$_2$), 2.8–3.1 (4H, m, 2CH$_2$), 4.04 (2H, t, CH$_2$), 6.8–7.3 (6H, m, arom-H) MS (FAB): 483 (M-H)$^-$

EXAMPLE 12

Synthesis of 2-isopentyloxy-2'-hydroxy-5, 5'-bis (2-carboxyethyl) biphenyl

To 3.09 ml of an ethanol solution containing 176.1 mg (0.3862 mmol) of 2-isopentyloxy-2'-hydroxy-5, 5'-bis (2ethoxycarbonylethyl) biphenyl obtained in Reference Example 12, 3.09 ml (3.09 mmol) of 1 N sodium hydroxide solution was added and the mixture was agitated at room temperature for 22.5 hours. The solvent of the reaction mixture was evaporated off under reduced pressure and, to the resulting evaporated residue, water was added. The solution obtained was washed with ether and was then acidified using 1 N hydrochloric acid and then 0.1 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 153.1 mg (0.3828 mmol, 99%) of 2-isopentyloxy-2'-hydroxy-5,5'-bis (2-carboxyethyl) biphenyl was obtained as an oily product. $^1$H-NMR (CDCl$_3$) δ (ppm): 0.88 (6H, d, (CH$_3$)$_2$), 1.6–1.9 ('6H, m, CH$_2$, CH), 2.5–2.8 (4H, m, 2CH$_2$), 2.8–3.1 (4H, m, 2CH$_2$), 4.06 (2H, t, CH$_2$), 6.8–7.3 (6H, m, arom-H) MS (FAB): 399 (M-H)$^-$

EXAMPLE 13

Synthesis of 2-(3-carboxypropoxy)-2'-hydroxy-5, 5'-bis (2-carboxyethyl) biphenyl To 6.9 ml of an ethanol solution containing 86.3 mg (0.1726 mmol) of 2-(3-ethoxycarbonylpropoxy)-2'- hydroxy-5, 5'-bis (2-ethoxycarbonylethyl) biphenyl obtained in Reference Example 13, 1.38 ml (1.38 mmol) of 1 N sodium hydroxide solution was added and the mixture was agitated at room temperature for 63 hours. The solvent of the reaction mixture was evaporated off under reduced pressure and, to the resulting evaporated residue, water was added. The solution obtained was washed with ether and was then acidified using 1 N hydrochloric acid and then 0.1 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 67.7 mg (0.1627 mmol, 94%) of 2-(3-carboxypropoxy)-2'-hydroxy-5,5'-bis (2-carboxyethyl) biphenyl was obtained as an oily product. $^1$H-NMR (MeOH-$d_4$) δ (ppm): 1.8–2.1 (2H, m, $CH_2$), 2.2–2.5 (2H, m, $CH_2$), 2.5–2.8 (4H, m, $2CH_2$), 2.8–3.1 (4H, m, $2CH_2$), 3.97 (2H, t, $CH_2$), 6.7–7.2 (6H, m, arom-H) MS (FAB): 415 (M-H)$^-$

EXAMPLE 14

Synthesis of 2-phenethyloxy-2'-hydroxy-5, 5'-bis (2-carboxyethyl) biphenyl

To 12.2 ml of an ethanol solution containing 186.6 mg (0.3808 mmol) of 2-phenethyloxy-2'-hydroxy-5, 5'-bis(2-ethoxycarbonylethyl) biphenyl obtained in Reference Example 14, 3.05 ml (3.05 mmol) of 1 N sodium hydroxide solution was added and the mixture was agitated at room temperature for 22 hours. The solvent of the reaction mixture was evaporated off under reduced pressure and, to the resulting evaporated residue, water was added. The solution obtained was washed with ether and was then acidified using 1 N hydrochloric acid and then 0.1 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 158.7 mg (0.3656 mmol, 96%) of 2-phenethyloxy-2'-hydroxy-5,5'-bis (2-carboxyethyl) biphenyl was obtained as an oily product. $^1$H-NMR (CDCl$_3$) δ (ppm): 2.5–2.8 (4H, m, $2CH_2$), 2.8–3.1 (6H, m, $3CH_2$), 4.22 (2H, t, $CH_2$), 6.8–7.3 (11H, m, arom-H) MS (FAB): 433 (M-H)$^-$

EXAMPLE 15

Synthesis of 2-cyclohexyloxy-2'-hydroxy-5, 5'-bis (2-carboxyethyl) biphenyl

To 1.32 ml of an ethanol solution containing 24.6 mg (0.0526 mmol) of 2-cyclohexyloxy-2'-hydroxy-5, 5'-bis (2-ethoxycarbonylethyl) biphenyl obtained in Reference Example 15, 0.263 ml (0.263 mmol) of 1 N sodium hydroxide solution was added and the mixture was agitated at room temperature for 47 hours. The solvent of the reaction mixture was evaporated off under reduced pressure and, to the resulting evaporated residue, water was added. The solution obtained was washed with ether and was then acidified using 1 N hydrochloric acid and then 0.1 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 21.6 mg (0.0524 mmol, 99%) of 2-cyclohexyloxy-2'-hydroxy-5,5'-bis (2-carboxyethyl) biphenyl was obtained as an oily product. $^1$H-NMR (CDCl$_3$) δ (ppm): 1.0–2.0 (10H, m, cyclohexyl-$5CH_2$), 2.5–2.8 (4H, m, $2CH_2$), 2.8–3.1 (4H, m, $2CH_2$), 4.0–4.4 (1H, m, cyclohexyl-CH), 6.8–7.3 (6H, m, arom-H) MS (FAB): 411 (M-H)$^-$

REFERENCE EXAMPLE 16

Synthesis of 2-methoxy-2'-hydroxy-5,5'-bis (2-ethoxycarbonylethyl) biphenyl

To 5 ml of a DMF solution containing 200 mg (0.5181 mmol) of 2,2'-dihydroxy-5,5'-bis (2-ethoxycarbonylethyl) biphenyl and 0.3292 ml (5.181 mmol) of methyl iodide, there were added 85.8 mg (0.6217 mmol) of anhydrous potassium carbonate and a small amount of copper powder and the resulting mixture was agitated for 2 hours at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by a silica gel column chromatography (with 20 g of WAKO-gel C-200, eluent: toluene and toluene/ethyl acetate of 25/1) to obtain 188.9 mg (0.4723 mmol, 91%) of 2-methoxy-2'-hydroxy-5, 5'-bis(2-ethoxycarbonylethyl) biphenyl as an oily product. $^1$H-NMR (CDCl$_3$) δ (ppm): 1.24 (6H, t, $2CH_3$), 2.62 (4H, t, $2CH_2$), 2.9–3.0 (4H, m, $2CH_2$), 3.87 (3H, s, $CH_2$), 4.13 (4H, q, $2CH_2$), 6.13 (1H, s, OH), 6.9–7.3 (6H, m, arom-H) MS (FAB): 400 (M)$^+$

REFERENCE EXAMPLE 17

Synthesis of 2-ethoxy-2'-hydroxy-5,5'-bis (2-ethoxycarbonylethyl) biphenyl

To 5 ml of a DMF solution containing 200 mg (0.5181 mmol) of 2,2'-dihydroxy-5,5'-bis (2-ethoxycarbonylethyl) biphenyl and 0.423 ml (5.181 mmol) of ethyl iodide, there were added 85.8 mg (0.6217 mmol) of anhydrous potassium carbonate and a small amount of copper powder and the resulting mixture was agitated overnight at room temperature. The reaction mixture was filtered by suction through Celite to remove the solid matte rand the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel column chromatography (with 20 g of WAKO-gel C-200, eluent: toluene and toluene/ethyl acetate of 100/1 and 75/1) to obtain 141.6 mg (0.3420 mmol, 66%) of 2-ethoxy-2'-hydroxy-5,5'-bis (2-ethoxycarbonylethyl) biphenyl as an oily product. $^1$H-NMR (CDCl$_3$) δ (ppm): 1.24 (6H, t, $2CH_3$), 1.36 (3H, t, $CH_3$), 2.62 (2H, t, $CH_2$), 2.63 (2H, t, $CH_2$), 2.94 (2H, t, $CH_2$), 2.95 (2H, t, $CH_2$), 4.11 ('6H, q, $CH_2$), 4.13 (4H, q, $2CH_2$), 6.66 (1H, s, OH), 6.9–7.3 (6H, m, arom-H) MS (FAB): 414 (M$^+$)

EXAMPLE 16

Synthesis of 2-methoxy-2'-hydroxy-5,5'-bis (2-carboxyethyl) biphenyl

To 10 ml of an ethanol solution containing 160.9 mg (0.4023 mmol) of 2-methoxy-2'-hydroxy-5, 5'-bis (2-ethoxycarbonylethyl) biphenyl obtained in Reference Example 16, 3.22 ml (3.218 mmol) of 1 N sodium hydroxide solution was added and the mixture was agitated at room temperature overnight. The solvent of the reaction mixture was evaporated off under reduced pressure and, to the resulting evaporated residue, water was added. The solution obtained was acidified using 1 N hydrochloric acid to a pH of about 1–2. The thus-formed precipitate was filtered, washed with water and was then dried. 135.6 mg (0.3942 mmol, 98%) of 2-methoxy-2'-hydroxy-5, 5'-bis(2-carboxyethyl) biphenyl was obtained as a white solid. $^1$H-NMR (CDCl$_3$) δ (ppm): 2.6–2.7 (4H, m, 2CH$_2$), 2.9–3.0 (4H, m, 2CH$_2$), 3.90 (3H, s, CH$_3$), 6.9–7.3 (6H, m, arom-H) MS (FAB): 344 (M+)

EXAMPLE 17

Synthesis of 2-ethoxy-2'-hydroxy-5,5'-bis (2-carboxyethyl) biphenyl

To 8 ml of an ethanol solution containing 139.3 mg (0.3365 mmol) of 2-ethoxy-2'-hydroxy-5, 5'-bis (2-ethoxycarbonylethyl) biphenyl obtained in Reference Example 17, 2.69 ml (2.692 mmol) of 1 N sodium hydroxide solution was added and the mixture was agitated at room temperature overnight. The solvent of the reaction mixture was evaporated off under reduced pressure and, to the resulting evaporated residue, water was added. The solution obtained was acidified using 1 N hydrochloric acid to a pH of about 1–2. The thus-formed precipitate was filtered, washed with water and was then dried to obtain 95.1 mg (0.2656 mmol, 79%) of 2-ethoxy-2'-hydroxy-5, 5,'-bis (2-carboxyethyl) biphenyl as a white solid product. $^1$H-NMR (CDCl$_3$) δ (ppm): 1.38 (3H, t, CH$_3$), 2.6–2.7 (4H, m, 2CH$_2$), 2.9–3.0 (4H, m, 2CH$_2$), 4.13 (2H, q, CH$_2$), 6.9–7.3 (6H, m, arom-H) MS (FAB): 358 (M+)

REFERENCE EXAMPLE 18

Synthesis of 2,2'-dihydroxy-5,5'-bis (3-carboxypropyl) biphenyl

A mixture of pyridine (30 ml) and conc. hydrochloric acid (30 ml) was heated at about 180° C. for 30 mins. A known compound, 2,2'-dimethoxy-5,5'-bis (3-carboxypropyl) biphenyl (1.2 g) was added thereto and the mixture was heated at about 180° C. with stirring overnight. Upon cooling, the reaction mixture was poured into ice water and the mixture was extracted with ethyl acetate under acidic conditions with hydrochloric acid. The ethyl acetate layer was washed with aqueous saturated sodium chloride, dried by adding anhydrous magnesium sulfate, then the solvent was evaporated off under reduced pressure. A residue was re-precipitated by adding ethyl acetate-toluene to obtain 2,2'-dihydroxy-5,5'-bis (3-carboxypropyl) biphenyl (1.01 g, 91%) as a white powder. $^1$H-NMR (CD$_3$OD) δ (ppm): 1.8–2.1 (4H, m, 2CH$_2$), 2.32 (4H, t, 2CH$_2$), 2.63 (4H, t, 2CH$_2$), 6.84 (2H, d, arom-H), 6.9–7.2 (4H, m, arom-H) MS (FAB): 357 (M-H)−

REFERENCE EXAMPLE 19

Synthesis of 2,2'-dihydroxy-5,5'-bis (3-methoxycarbonylpropyl) biphenyl

Thionyl chloride (0.208 ml, 2.793 mmol) was dropwise added to 2,2'-dihydroxy-5,5'-bis (3-carboxypropyl) biphenyl (100 mg, 0.2793 mmol) obtained in Reference Example 18, dissolved in methanol (2 ml) under cooling. The reaction mixture was stirred for several minutes and further agitated at room temperature for 1.5 hours. Solvent in the reaction mixture was evaporated off under reduced pressure, then the residue was dissolved in chloroform. The chloroform solution was washed with aqueous sodium bicarbonate, water and aqueous sodium chloride in this order, then dried by adding anhydrous sodium sulfate. The residue obtained by evaporating off the solvent was purified by silica-gel column chromatography (with 10 g of WAKO-gel C-200, eluent: toluene and toluene/ethyl acetate of 20/1) to obtain 101.2 mg (0.2622 mmol, 94%) of 2,2'-dihydroxy-5,5'-bis (3-methoxycarbonylpropyl) biphenyl as an oily product. $^1$H-NMR (CDCl$_3$) δ (ppm): 1.95 (4H, m, 2CH$_2$), 2.35 (4H, t, 2CH$_2$), 2.63 (4H, t, 2CH$_2$), 3.62 (6H, s, 2CH$_3$), 6.07 (2H, s, 2OH), 6.8–7.3 (6H, m, arom-H), MS (FAB): 385 (M-H)−

REFERENCE EXAMPLE 20

Synthesis of 2,2'-dihydroxy-5,5'-bis (3-ethoxycarbonylpropyl) biphenyl

Thionyl chloride (1.1 ml, 13.97 mmol) was dropwise added under cooling into 2,2'-dihydroxy-5,5'-bis (3-carboxypropyl) biphenyl (500 mg, 1.3966 mmol), obtained in Reference Example 18, dissolved in ethanol (50 ml). After agitating several minutes, the reaction mixture was stirred at room temperature for 2 hours. Solvent in the reaction mixture was evaporated off under reduced pressure, and the residue was dissolved in chloroform. This solution was washed with dilute aqueous sodium bicarbonate, water and aqueous sodium chloride in this sequence and was dried by adding anhydrous sodium sulfate. The residue obtained after the solvent had been evaporated off was purified by silica-gel column chromatography (with 75 g of WAKO-gel C-200, eluent: chloroform and chloroform/methanol of 100/1) to obtain 435 mg (1.0507 mmol, 75%) of 2,2'-dihydroxy-5,5'-bis (3-ethoxycarbonylpropyl) biphenyl as an oily product. $^1$H-NMR (CDCl$_3$) δ (ppm): 1.25 (6H, t, 2CH$_3$), 1.9–2.1 (4H, m, 2CH$_2$), 2.35 (4H, t, 2CH$_2$), 2.65 (4H, t, 2CH$_2$), 4.09 (4H, t, 2CH$_2$), 5.86 (2H, s, 2OH), 6.9–7.2 (6H, m, arom-H), MS (FAB): 413 (M-H)−

REFERENCE EXAMPLE 21

Synthesis of 2-benyloxy-2'-hydroxy-5,5'-bis (3-ethoxycarbonylpropyl) biphenyl

To 5 ml of a DMF solution containing 200 mg (0.4831 mmol) of 2,2'-dihydroxy-5,5'-bis (3-ethoxycarbonylpropyl) biphenyl and 0.200 ml (1.681 mmol) of benzyl bromide, there were added 83 mg (0.6014 mmol) of anhydrous potassium carbonate and a small amount of copper powder and the resulting mixture was agitated for 1 hour at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel chromatography (with 20 g of WAKO-gel C-200, eluent: chloroform) to obtain 208 mg (0.4127 mmol, 85%) of 2-benzyloxy-2'-hydroxy-5,5'-bis (2-ethoxycarbonylpropyl) biphenyl as an oily product. $^1$H-NMR (CDCl$_3$) δ (ppm): 1.24 (6H, t, 2CH$_3$), 1.7–2.2 (4H, m, 2CH$_2$), 2.34 (4H, t, 2CH$_2$), 2.64 (4H, t, 2CH$_2$), 4.10 (2H, q, CH$_2$), 4.12 (2H, q, CH$_2$), 5.07 (2H, s, CH$_2$), 6.32 (1H, s, OH), 6.8–7.3 (11H, m, arom-H) MS (FAB): 503 (M-H)$^-$

REFERENCE EXAMPLE 22

Synthesis of 2-(2-fluoro-4-bromobenzyloxy)-2'-hydroxy-5, 5'-bis (3-methoxycarbonylpropyl) biphenyl To 5 ml of a DMF solution containing 200 mg (0.5181 mmol) of 2,2'-dihydroxy-5,5'-bis (3-methoxycarbonylpropyl) biphenyl and 0.731 ml (5.181 mmol) of 2-fluoro-4-bromobenzyl bromide, there were added 85.8 mg (0.6217 mmol) of anhydrous potassium carbonate and the resulting mixture was agitated for 2 hours at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel column chromatography (with 15 g of WAKO-gel C-200, eluent: toluene and toluene/ethyl acetate of 100/1) to obtain 248.1 mg (0.4322 mmol), 83%) of 2-(2-fluoro-4-bromobenzyloxy)-2'-hydroxy-5, 5'-bis(3-methoxycarbonylpropyl) biphenyl as an oily product. $^1$H-NMR (CDCl$_3$) δ (ppm): 1.7–2.2 (4H, m, 2CH$_3$), 2.35 (4H, t, 2CH$_2$), 2.67 (4H, t, 2CH$_2$), 3.66 (6H, s, 2CH$_3$), 5.03 (2H, s, CH$_2$), 6.87 (1H, s, OH), 6.8–7.3 (9H, m, arom-H), MS (FAB): 573 (M-H)$^-$

REFERENCE EXAMPLE 23

Synthesis of 2-cyclohexylmethoxy-2'-hydroxy-5, 5'-bis (3-methoxycarbonylpropyl) biphenyl To 5 ml of a DMF solution containing 200 mg (0.5181 mmol) of 2,2'-dihydroxy-5,5'-bis (3-methoxycarbonylpropyl) biphenyl and 1.46 ml (10.362 mmol) of cyclohexylmethyl bromide, there were added 85.8 mg (0.6217 mmol) of anhydrous potassium carbonate and a small amount of copper powder and the resulting mixture was agitated overnight at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel column chromatography (with 15 g of WAKO-gel C-200, eluent: toluene and toluene/ethyl acetate of 50/1) to obtain 215 mg (0.4454 mmol, 86%) of 2-cyclohexylmethoxy-2'-hydroxy-5,5'-bis (3-methoxycarbonylpropyl) biphenyl as an oily product. $^1$H-NMR (CDCl$_3$) δ (ppm): 0.6–2.2 (15H, m, cyclohexyl-H, 2CH$_2$), 2.36 (4H, t, 2CH$_2$), 2.65 (4H, t, 2CH$_2$), 3.66 (6H, s, 2CH$_3$), 3.81 (2H, d, CH$_2$), 6.52 (1H, s, OH), 6.8–7.3 (6H, m, arom-H) MS (FAB): 482 (M$^+$)

REFERENCE EXAMPLE 24

Synthesis of 2-methoxy-2'-hydroxy-5,5'-bis (3-methoxycarbonylpropyl) biphenyl

To 5 ml of a DMF solution containing 200 mg (0.5181 mmol) of 2,2'-dihydroxy-5,5'-bis (3-methoxycarbonylpropyl) biphenyl and 0.329 ml (5.181 mmol) of methyl iodide, there were added 85.5 mg (0.6217 mmol) of anhydrous potassium carbonate and a small amount of copper powder and the resulting mixture was agitated for 4 hours at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous adding anhydrous sodium sulfate. The residue obtained after the solvent had been evaporated off was purified by silica gel column chromatography (with 20 g of WAKO-gel C-200, eluent: toluene and toluene/ethyl acetate of 50/1 and 25/1) to obtain 159 mg (0.3975 mmol, 77%) of 2-methoxy-2'-hydroxy-5,5'-bis (3-methoxycarbonylpropyl) biphenyl as an oily product. $^1$H-NMR (CDCl$_3$) δ (ppm): 1.96 (4H, m, 2CH$_2$), 2.35 (2H, t, CH$_2$), 2.36 (2H, t, CH$_2$), 2.63 (2H, t, CH$_2$), 2.66 (2H, t, CH$_2$), 3.66 (6H, s, 2CH$_3$), 3.87 (3H, s, CH$_3$), 6.24 (1H, s, OH), 6.9–7.3 (6H, m, arom-H) MS (FAB): 400 (M$^+$)

REFERENCE EXAMPLE 25

Synthesis of 2-ethoxy-2'-hydroxy-5,5'-bis (3-methoxycarbonylpropyl) biphenyl

To 5 ml of a DMF solution containing 200 mg (0.5181 mmol) of 2,2'-dihydroxy-5,5'-bis (3-methoxycarbonylpropyl) biphenyl and 0.391 ml (5.181 mmol) of ethyl bromide, there were added 85.8 mg (0.6217 mmol) of anhydrous potassium carbonate and a small amount of copper powder and the resulting mixture was agitated for 5 hours at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel column chromatography (with 15 g of WAKO-gel C-200, eluent: toluene and toluene/ethyl acetate of 100/1) to obtain 184 mg (0.4444 mmol, 86%) of 2-ethoxy-2'-hydroxy-5, 5'-bis (3-methoxycarbonylpropyl) biphenyl as an oily product. $^1$H-NMR (CDCl$_3$) δ (ppm): 1.36 (3H, t, CH$_3$), 1.7–2.2 (4H, m, 2CH$_2$), 2.36 (4H, t, 2CH$_2$), 2.64 (4H, t, 2CH$_2$), 3.66 (6H, s, 2CH$_3$), 4.10 (2H, q, CH$_2$), 6.66 (1H, s, OH), 6.8–7.3 (6H, m, arom-H) MS (FAB): 413 (M$^+$)

REFERENCE EXAMPLE 26

Synthesis of 2-propoxy-2'-hydroxy-5,5'-bis (3-methoxycarbonylpropyl) biphenyl

To 5 ml of a DMF solution containing 200 mg (0.5181 mmol) of 2,2'-dihydroxy-5,5'-bis (3-methoxycarbonylpropyl) biphenyl and 0.475 ml (5.181 mmol) of propyl bromide, there were added 85.8 mg (0.6217 mmol) of anhydrous potassium carbonate and a small amount of copper powder and the resulting mixture was agitated for 5 hours at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel column chromatography (with 20 g of WAKO-gel C-200, eluent: toluene and toluene/ethyl acetate of 50/1) to obtain 202 mg (0.4720 mmol, 91%) of 2-propoxy-2'-hydroxy-5,5'-bis (3-methoxycarbonylpropyl) biphenyl as an oily product. $^1$H-NMR (CDCl$_3$) δ (ppm): 0.94 (3H, t, CH$_3$), 1.6–2.2 (6H, m, 3CH$_2$), 2.36 (4H, t, 2CH$_2$), 2.65 (4H, t, 2CH$_2$), 3.66 (6H, s, 2CH$_3$), 3.99 (2H, t, CH$_2$), 6.60 (1H, s, OH), 6.8–7.3 (6H, m, arom-H) MS (FAB): 427 (M-H)$^-$

REFERENCE EXAMPLE 27

Synthesis of 2-butoxy-2'-hydroxy-5,5'-bis (3-methoxycarbonylpropyl) biphenyl

To 5 ml of a DMF solution containing 200 mg (0.5181 mmol) of 2,2'-dihydroxy-5,5'-bis (3-methoxycarbonylpropyl) biphenyl and 0.562 ml (5.181 mmol) of butyl bromide, there were added 85.8 mg (0.6217 mmol) of anhydrous potassium carbonate and a small amount of copper powder and the resulting mixture was agitated for 4 hours at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel column chromatography (with 20 g of WAKO-gel C-200, eluent: toluene and toluene/ethyl acetate of 50/1) to obtain 190 mg (0.4299 mmol), 83%) of 2-butoxy-2'-hydroxy-5,5'-bis (3-methoxycarbonylpropyl) biphenyl as an oily product. $^1$H-NMR (CDCl$_3$) δ (ppm): 0.88 (3H, t, CH$_3$), 1.1–2.2 (8H, m, 4CH$_2$), 2.36 (4H, t, 2CH$_2$), 2.65 (4H, t, 2CH$_2$), 3.66 (6H, s, 2CH$_3$), 4.02 (2H, t, CH$_2$), 6.59 (1H, s, OH), 6.8–7.3 (6H, m, arom-H) MS (FAB): 441 (M-H)$^-$

REFERENCE EXAMPLE 28

Synthesis of 2-heptyloxy-2'-hydroxy-5,5'-bis (3-methoxycarbonylpropyl) biphenyl

To 5 ml of a DMF solution containing 200 mg (0.5181 mmol) of 2,2'-dihydroxy-5,5'-bis (3-methoxycarbonylpropyl) biphenyl and 0.840 ml (5.181 mmol) of heptyl bromide, there were added 85.8 mg (0.6217 mmol) of anhydrous potassium carbonate and a small amount of copper powder and the resulting mixture was agitated for 5 hours at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel column chromatography (with 15 g of WAKO-gel C-200, eluent: toluene and toluene/ethyl acetate of 50/) to obtain 224 mg (0.4628 mmol, 89%) of 2-heptyloxy-2'-hydroxy-5,5'-bis (3-methoxycarbonylpropyl) biphenyl as an oily product. $^1$H-NMR (CDCl$_3$) δ (ppm): 0.85 (3H, t, CH$_3$), 1.0–2.2 (14H, m, 7CH$_2$), 2.35 (4H, t, 2CH$_2$), 2.64 (4H, t, 2CH$_2$), 3.66 (6H, s, 2CH$_3$), 4.01 (2H, s, CH$_2$), 6.61 (1H, s, OH), 6.8–7.3 (6H, m, arom-H) MS (FAB): 483 (M-H)$^-$

REFERENCE EXAMPLE 29

Synthesis of 2-octyloxy-2'-hydroxy-5,5'-bis (3-methoxycarbonylpropyl) biphenyl

To 5 ml of a DMF solution containing 200 mg (0.5181 mmol) of 2,2'-dihydroxy-5,5'-bis (3-methoxycarbonylpropyl) biphenyl and 0.895 ml (5.181 mmol) of octyl bromide, there were added 85.8 mg (0.6217 mmol) of anhydrous potassium carbonate and a small amount of copper powder and the resulting mixture was agitated for 5 hours at room temperature. The reaction mixture was filtered by suction through Celite to remove the solid matter and the filtrate was washed with ethyl acetate. After the solvent in the filtrate was evaporated off under reduced pressure, the evaporated residue was dissolve din chloroform. This solution was washed with dilute hydrochloric acid, dilute aqueous sodium bicarbonate, water and aqueous sodium chloride solution in this sequence and was dried by adding anhydrous sodium sulfate. The residue obtained after the solvent had been evaporated off was purified by silica gel column chromatography (with 15 g of WAKO-gel C-200, eluent: toluene and toluene/ethyl acetate of 100/1) to obtain 236 mg (0.4738 mmol, 91%) of 2-octyloxy-2'-hydroxy-5,5'-bis (3-methoxycarbonylpropyl) biphenyl as an oily product. $^1$H-NMR (CDCl$_3$) δ (ppm): 0.87 (3H, t, CH$_3$), 1.0–2.2 (16H, m, 8CH$_2$), 2.36 (4H, t, 2CH$_2$), 2.65 (4H, t, 2CH$_2$), 3.66 (6H, s, 2CH$_3$), 4.01 (2H, t, CH$_2$), 6.61 (1H, s, OH), 6.8–7.3 (6H, m, arom-H) MS (FAB): 497 (M-H)$^-$

REFERENCE EXAMPLE 30

Synthesis of 2-isopentyloxy-2'-hydroxy-5, 5'-bis (3methoxycarbonylpropyl) biphenyl To 5 ml of a DMF solution containing 200 mg (0.5181 mmol) of 2,2'-dihydroxy-5,5'-bis (3-methoxycarbonylpropyl) biphenyl and 0.646 ml (5.181 mmol) of isopentyl bromide, there were added 85.8 mg (0.6217 mmol) of anhydrous potassium carbonate and a small amount of copper powder and the resulting mixture was agitated for 5 hours at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric acid, dilute aqueous sodium bicarbonate, water and aqueous sodium chloride solution in this sequence and was dried by adding anhydrous sodium sulfate., The residue obtained after the solvent had been evaporated off was purified by silica gel column chromatography (with 15 g of WAKO-gel C-200, eluent: toluene and toluene/ethyl acetate of 50/1) to obtain 1908 mg (0.4342 mmol, 84%) of 2-isopentyloxy-2'-hydroxy-5,5'-bis (3-methoxycarbonylpropyl) biphenyl as an oily product. $^1$H-NMR (CDCl$_3$) δ (ppm): 0.86 (6H, d, 2CH$_3$), 1.0–2.2 (7H, m, CH, 3CH$_2$), 2.35 (4H, t, 2CH$_2$), 2.64 (4H, t, 2CH$_2$), 3.66 (6H, s, 2CH$_3$), 4.04 (2H, t, CH$_2$), 6.58 (1H, s, OH), 6.8–7.3 (6H, m, arom-H) MS (FAB): 455 (M-H)$^-$

REFERENCE EXAMPLE 31

Synthesis of 2-(3-chloropropoxy)-2'-hydroxy-5, 5'-bis (3-methoxycarbonylpropyl) biphenyl To 5 ml of a DMF solution containing 200 mg (0.5181 mmol) of 2,2'-dihydroxy-5,5'-bis (3-methoxycarbonylpropyl) biphenyl and 0.646 ml (5.181 mmol) of 1-bromochloropropane, there were added 85.8 mg (0.6217 mmol) of anhydrous potassium carbonate and a small amount of copper powder and the resulting mixture was agitated for 5 hours at room temperature. The reaction mixture was filtered by suction through Celite to remove the solid matter and the filtrate was washed with ethyl acetate. After the solvent in the filtrate was evaporated off under reduced pressure, the evaporated residue was dissolved in chloroform. This solution was washed with dilute hydrochloric sodium chloride solution in this sequence and was dried by adding anhydrous sodium sulfate. The residue obtained after the solvent had been evaporated off was purified by silica gel column chromatography (with 15 g of WAKO-gel C-200, eluent: toluene and toluene/ethyl acetate of 100/1) to obtain 206 mg (0.4454 mmol, 86%) of 2-(3-chloropropoxy-2'-hydroxy-5,5'-bis (3-methoxycarbonylpropyl) biphenyl as an oily product. $^1$H-NMR (CDCl$_3$) δ (ppm): 1.8–2.2 (6H, m, 3CH$_2$), 2.36 (4H, t, 2CH$_2$), 2.5–2.8 (4H, m, 2CH$_2$), 3.51 (2H, t, CH$_2$), 3.66 (6H, s, 2CH$_3$), 4.16 (2H, t, CH$_2$), 6.05 (1H, s, OH), 6.8–7.3 (6H, m, arom-H) MS (FAB): 461 (M-H)$^-$

EXAMPLE 18

Synthesis of 2-benzyloxy-2'-hydroxy-5,5'-bis (3-carboxypropyl) biphenyl

To 3.1 ml of a methanol solution containing 130 mg (0.2579 mmol) of 2-benzyloxy-2'-hydroxy-5, 5'-bis (3-ethoxycarbonylpropyl) biphenyl obtained in Reference Example 21, 2.0 ml (2.000 mmol) of 1 N sodium hydroxide solution were added and the mixture was agitated at room temperature for 2 days. The solvent of the reaction mixture was evaporated off under reduced pressure and, to the resulting evaporated residue, water was added. The solution obtained was washed with ether and was then acidified using 1 N hydrochloric acid and then 0.1 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 103 mg (0.2299 mmol, 89%) of 2-benzyloxy-2'-hydroxy-5,5'-bis (3-carboxypropyl) biphenyl was obtained as an oily product. $^1$H-NMR (MeOH-d$_4$) δ (ppm): 1.7–2.2 (4H, m, 2CH$_2$), 2.2–2.4 (4H, m, 2CH$_2$), 2.4–2.7 (4H, m, 2CH$_2$), 5.01 (2H, s, CH$_2$), 6.7–7.3 (11H, m, arom-H) MS (FAB): 447 (M-H)$^-$

EXAMPLE 19

Synthesis of 2-(2-fluoro-4-bromobenzyloxy)-2'-hydroxy-5, 5'-bis (3-carboxypropyl) biphenyl To 13 ml of a methanol solution containing 233.2 mg (0.4062 mmol) of 2-(2-fluoro-4-bromobenzyloxy-2'-hydroxy-5, 5'-bis (3-methoxycarbonylpropyl) biphenyl obtained in Reference Example 22, 3.25 ml (3.25 mmol) of 1 N sodium hydroxide solution were added and the mixture was agitated at room temperature for 2 days. The solvent of the reaction mixture was evaporated off under reduced pressure and, to the resulting evaporated residue, water was added. The solution obtained was washed with ether and was then acidified using 1 N hydrochloric acid and then 0.1 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 208.5 mg (0.3819 mmol, 94%) of 2-fluoro-4-bromobenzyloxy)-2'-hydroxy-5, 5'-bis (3-carboxypropyl) biphenyl were obtained as an oily product. $^1$H-NMR (CDCl$_3$) δ (ppm): 1.8–2.2 (4H, m, 2CH$_2$), 2.38 (4H, t, 2CH$_2$), 2.66 (4H, t, 2CH$_2$), 5.05 (2H, s, CH$_2$), 6.8–7.3 (9H, m, arom-H) MS (FAB): 545 (M-H)$^-$

EXAMPLE 20

Synthesis of 2-cyclohexylmethoxy-2'-hydroxy-5, 5'-bis (3-carboxypropyl) biphenyl To 13 ml of a methanol solution containing 93.3 mg (0.1936 mmol) of 2-cyclohexylmethoxy-2'-hydroxy-5, 5'-bis (3-methoxycarbonylpropyl) biphenyl obtained in Reference Example 23, 3.3 ml (3.3 mmol) of 1 N sodium hydroxide solution was added and the mixture was agitated at room temperature for 2 days. The solvent of the reaction mixture was evaporated off under reduced pressure and, to the resulting evaporated residue, water was added. The solution obtained was washed with ether and was then acidified using 1 N hydrochloric acid and then 0.1 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 181 mg (0.3986 mmol, 97%) of 2-cyclohexylmethoxy-2'-hydroxy-5,5'-bis (3-carboxypropyl) biphenyl was obtained as an oily product. $^1$H-NMR (CDCl$_3$) δ (ppm): 0.6–2.2 (15H, m, cyclohexyl-H, 2CH$_2$), 2.38 (4H, t, 2CH$_2$), 2.69 (4H, t, 2CH$_2$), 3.81 (2H, d, CH$_2$), 6.8–7.3 (6H, m, arom-H) MS (FAB): 453 (M-H)$^-$

EXAMPLE 21

Synthesis of 2-methoxy-2'-hydroxy-5,5'-bis (3-carboxypropyl) biphenyl

To 4.3 ml of an ethanol solution containing 143.5 mg (0.3588 mmol) of 2-methoxy-2'-hydroxy-5, 5'-bis (3-methoxycarbonylpropyl) biphenyl obtained in Reference Example 24, 1.4 ml (1.4 mmol) of 1 N sodium hydroxide solution was added and the mixture was agitated at room temperature for 3 days. The solvent of the reaction mixture was evaporated off under reduced pressure and, to the resulting evaporated residue, water was added. The solution obtained was washed with ether and was then acidified using 1 N hydrochloric acid and then 0.1 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 125.7 mg (0.3379 mmol, 94%) of 2-methoxy-2'-hydroxy-5,5'-bis (3-carboxypropyl) biphenyl was obtained as an oily product. $^1$H-NMR (CDCl$_3$) δ (ppm): 1.97 (4H, m, 2CH$_2$), 2.39 (4H, t, 2CH$_2$), 2.68 (2H, t, CH$_2$), 2.69 (2H, t, CH$_2$), 3.88 (3H, s, CH$_3$), 6.9–7.3 (6H, m, arom-H) MS (FAB): 372 (M)+

EXAMPLE 22

Synthesis of 2-ethoxy-2'-hydroxy-5,5'-bis (3-carboxypropyl) biphenyl

To 14 ml of an ethanol solution containing 171.2 mg (0.43355 mmol) of 2-ethoxy-2'-hydroxy-5, 5'-bis (3-methoxycarbonylpropyl) biphenyl obtained in Reference Example 25, 3.3 ml (3.3 mmol) of 1 N sodium hydroxide solution was added and the mixture was agitated at room temperature for 2 days. The solvent of the reaction mixture was evaporated off under reduced pressure and, to the resulting evaporated residue, water was added. The solution obtained was washed with ether and was then acidified using 1 N hydrochloric acid and then 0.2 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 160 mg (0.4145 mmol, 96%) of 2-ethoxy-2'-hydroxy-5,5'-bis (3-carboxypropyl) biphenyl was obtained as a oily product. $^1$H-NMR (CDCl$_3$) δ (ppm): 1.25 (3H, t, CH$_3$), 1.8–2.2 (4H, m, 2CH$_2$), 2.40 (4H, t, 2CH$_2$), 2.69 (4H, t, 2CH$_2$), 4.12 (2H, q, CH$_2$), 6.8–7.3 (6H, m, arom-H) MS (FAB): 385 (M-H)−

EXAMPLE 23

Synthesis of 2-cyclohexylmethoxy-2'-hydroxy-5, 5'-bis (2-carboxypropyl) biphenyl To 20 ml of a methanol solution containing 198.5 mg (0.4638 mmol) of 2-propoxy-2'-hydroxy-5, 5'-bis (3-methoxycarbonylpropyl) biphenyl obtained in Reference Example 26, 3.7 ml (3.7 mmol) of 1 N sodium hydroxide solution was added and the mixture was agitated at room temperature for 2 days. The solvent of the reaction mixture was evaporated off under reduced pressure and, to the resulting evaporated residue, water was added. The solution obtained was washed with ether and was then acidified using 1 N hydrochloric acid and then 0.1 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 182.7 mg (0.4568 mmol, 98%) of 2-propoxy-2'-hydroxy-5,5'-bis (3-carboxypropyl) biphenyl was obtained as an oily product. $^1$H-NMR (CDCl$_3$) δ (ppm): 0.93 (3H, t, CH$_3$), 1.5–2.2 (6H, m, 3CH$_2$), 2.38 (4H, t, 2CH$_2$), 2.67 (4H, t, 2CH$_2$), 3.98 (2H, t, CH$_2$), 6.8–7.3 (6H, m, arom-H) MS (FAB): 399 (M-H)−

EXAMPLE 24

Synthesis of 2-butoxy-2'-hydroxy-5,5'-bis (3-carboxypropyl) biphenyl

To 12 ml of a methanol solution containing 169.4 mg (0.3832 mmol) of 2-butoxy-2'-hydroxy-5, 5'-bis (3-methoxycarbonylpropyl) biphenyl obtained in Reference Example 27, 3.1 ml (3.1 mmol) of 1 N sodium hydroxide solution was added and the mixture was agitated at room temperature for 2 days. The solvent of the reaction mixture was evaporated off under reduced pressure and, to the resulting evaporated residue, water was added. The solution obtained was washed with ether and was then acidified using 1 N hydrochloric acid and then 0.1 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 155.4 mg (0.3753 mmol, 98%) of 2-butoxy-2'-hydroxy-5,5'-bis (3-carboxypropyl) biphenyl was obtained as an oily product. $^1$H-NMR (CDCl$_3$) δ (ppm): 0.88 (3H, t, CH$_3$), 1.1–2.2 (8H, m, 4CH$_2$), 2.39 (4H, t, 2CH$_2$), 2.68 (4H, t, 2CH$_2$), 4.03 (2H, t, CH$_2$), 6.8–7.3 (6H, m, arom-H) MS (FAB): 413 (M-H)−

EXAMPLE 25

Synthesis of 2-heptyloxy-2'-hydroxy-5,5'-bis (3-carboxypropyl) biphenyl

To 12 ml of a methanol solution containing 193.7 mg (0.4002 mmol) of 2-heptyloxy-2'-hydroxy-5, 5'-bis (3-methoxycarbonylpropyl) biphenyl obtained in Reference Example 28, 3.2 ml (3.2 mmol) of 1 N sodium hydroxide solution was added and the mixture was agitated at room temperature for 2 days. The solvent of the reaction mixture was evaporated off under reduced pressure and, to the resulting evaporated residue, water was added. The solution obtained was washed with ether and was then acidified using 1 N hydrochloric acid and then 0.1 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 178.5 mg (0.3914 mmol, 98%) of 2-heptyloxy-2'-hydroxy-5,5'-bis (3-carboxypropyl) biphenyl was obtained as an oily product. $^1$H-NMR (CDCl$_3$) δ (ppm): 0.85 (3H, t, CH$_3$), 1.0–2.2 (14H, m, 7CH$_2$), 2.39 (4H, t, 2CH$_2$), 2.68 (4H, t, 2CH$_2$), 4.02 (2H, t, CH$_2$), 6.8–7.3 (6H, m, arom-H) MS (FAB): 455 (M-H)−

EXAMPLE 26

Synthesis of 2-octyloxy-2'-hydroxy-5,5'-bis (3-carboxypropyl) biphenyl

To 14 ml of a methanol solution containing 210 mg (0.4220 mmol) of 2-n-octyloxy-2'-hydroxy-5, 5'-bis (3-methoxycarbonylpropyl) biphenyl obtained in Reference Example 29, 3.4 ml (3.4 mmol) of 1 N sodium hydroxide solution was added and the mixture was agitated at room temperature for 2 days. The solvent of the reaction mixture was evaporated off under reduced pressure and, to the resulting evaporated residue, water was added. The solution obtained was washed with ether and was then acidified using 1 N hydrochloric acid and then 0.1 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 197.4 mg (0.420 mmol, 99%) of 2-octyloxy-2'-hydroxy-5,5'-bis (3-carboxypropyl) biphenyl was obtained as an oily product. $^1$H-NMR (CDCl$_3$) δ (ppm): 0.86 (3H, t, CH$_3$), 1.0–2.2 (16H, m, 8CH$_2$), 2.39 (4H, t, 2CH$_2$), 2.69 (4H, t, 2CH$_2$), 4.02 (2H, t, CH$_2$), 6.8–7.3 (6H, m, arom-H) MS (FAB): 469 (M-H)$^-$

EXAMPLE 27

Synthesis of 2-isopentyloxy-2'-hydroxy-5, 5'-bis (3-carboxypropyl) biphenyl

To 12 ml of a methanol solution containing 182.4 mg (0.4000 mmol) of 2-isopentyloxy-2'-hydroxy-5, 5'-bis (3methoxycarbonylpropyl) biphenyl obtained in Reference Example 30, 3.2 ml (3.2 mmol) of 1 N sodium hydroxide solution was added and the mixture was agitated at roo temperature for 2 days. The solvent of the reaction mixture was evaporated off under reduced pressure and, to the resulting evaporated residue, water was added. The solution obtained was washed with ether and was then acidified using 1 N hydrochloric acid and then 0.1 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 160 mg (0.3865 mmol, 97%) of 2-isopentyloxy-2'-hydroxy-5,5'-bis (3-carboxypropyl) biphenyl was obtained as an oily product. $^1$H-NMR (CDCl$_3$) δ (ppm): 0.87 (6H, d, 2CH$_3$), 1.1–2.2 (7H, m, 3CH$_2$, CH), 2.39 (4H, t, 2CH$_2$), 2.69 (4H, t, 2CH$_2$), 4.05 (2H, t, CH$_2$), 6.8–7.3 (6H, m, arom-H) MS (FAB): 413 (M-H)$^-$

EXAMPLE 28

Synthesis of 2-(3-chloropropoxy)-2'-hydroxy-5, 5'-bis (3-carboxypropyl) biphenyl To 13 ml of a methanol solution containing 186.3 mg (0.4023 mmol) of 2-(3-chloropropoxy)-2'-hydroxy-5,5'-bis (3methoxycarbonylpropyl) biphenyl obtained in Reference Example 31, 3.2 ml (3.2 mmol) of 1 N sodium hydroxide solution was added and the mixture was agitated at room temperature for 2 days. The solvent of the reaction mixture was evaporated off under reduced pressure and, to the resulting evaporated residue, water was added. The solution obtained was washed with ether and was then acidified using 1 N hydrochloric acid and then 0.2 N hydrochloric acid to a pH of about 3. The thus-formed precipitate was extracted with ethyl acetate and the extract was washed with water and then with aqueous sodium chloride and was then dried by adding anhydrous sodium sulfate. By evaporating off the solvent, 174.5 mg (0.4011 mmol, 99%) of 2-(3-chloropropoxy)-2'-hydroxy-5,5'-bis (3-carboxypropyl) biphenyl was obtained as an oily product. $^1$H-NMR (CDCl$_3$) δ (ppm): 1.8–2.2 (6H, m, 3CH$_2$), 2.40 (4H, t, 2CH$_2$), 2.68 (4H, t, 2CH$_2$), 3.58 (2H, t, CH$_2$), 4.16 (2H, t, CH$_2$), 6.8–7.3 (6H, m, arom-H) MS (FAB): 433 (M-H)$^-$

EXAMPLE 29

Production of disodium salt of 2-methoxy-2'-hydroxy-5,5'-bis (3-carboxypropyl) biphenyl 372 mg (1 mmol) of a compound 2-methoxy-2'-hydroxy-5,5'-bis (3-carboxypropyl) biphenyl obtained in Example 21 were suspended in 50 ml of distilled water and the compound was dissolved by adding thereto 2 ml of 1 N NaOH aqueous solution. The solution was concentrated by evaporation under reduced pressure and was subjected to freeze-drying, whereby 415 mg of the title compound were obtained.

In the same manner, as above, the compounds of formula (I) produced in Examples 1–20 and 22–28 were able to be converted into each corresponding disodium salt.

EXAMPLE 30

Encapsulated Preparation

An encapsulated preparation was prepared by encapsulating 200 mg of the mixture o the following composition in each of a plurality of #1 capsules.

| Composition | |
|---|---|
| Disodium salt of 2-methoxy-2'-hydroxy-5,5'-bis (3-carboxypropyl) biphenyl | 50 mg |
| Lactose | 50 mg |
| Corn starch | 80 mg |
| Crystallized cellulose | 16 mg |
| Calcium stearate | 4 mg |

What is claimed is:

1. A compound of the formula

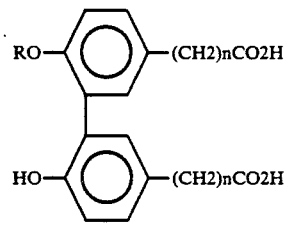

(I)

in which R is an alkyl of $C_{1-12}$,

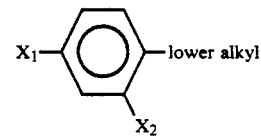

wherein $X_1$ and $X_2$ are same or different and are hydrogen or halogen, cyclohexylmethyl, cyclohexyl, tetrahydro-2H-pyran-1-yl-methyl, carboxy-lower or chloro-lower alkyl and n is 2 or 3, or a pharmaceutically acceptable salt thereof.

2. An aldose reductase inhibitor, comprising an effective amount of biphenyl-5,5'-bis-alkanoic acid derivative of the formula

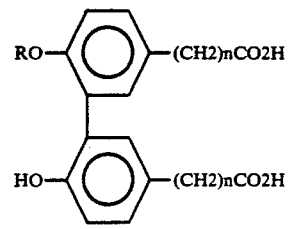

(I)

or a pharmaceutically acceptable salt thereof, in which

R denotes an alkyl of $C_{1-12}$,

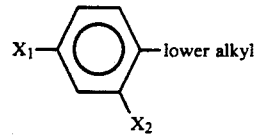

wherein $X_1$ and $X_2$ are same or different and are hydrogen or halogen, or cyclohexylmethyl, cyclohexyl, tetrahydro-2H-pyran-l-yl-methyl, carboxy-lower or chloro-lower alkyl and n is 2 or 3, in admixture with an excipient, said amount being effective to inhibit aldose reductase in a human patient.

* * * * *